United States Patent [19]

Ikeda et al.

[11] 4,008,219
[45] Feb. 15, 1977

[54] 4-BENZAZONINE DERIVATIVES AND PROCESS FOR PREPARATION THEREOF

[75] Inventors: Masao Ikeda; Shigeo Miyamoto; Thutomu Nozawa; Akira Kurobe, all of Toyama; Osamu Futsukaichi, Shinminato, all of Japan

[73] Assignee: Nihon Iyakuhin Kogyo Co., Ltd., Japan

[22] Filed: May 6, 1974

[21] Appl. No.: 467,520

[30] Foreign Application Priority Data

| May 8, 1973 | Japan | 48-51458 |
|---|---|---|
| May 8, 1973 | Japan | 48-51459 |
| May 8, 1973 | Japan | 48-51460 |
| May 8, 1973 | Japan | 48-51461 |
| Jan. 16, 1974 | Japan | 49-7683 |
| Feb. 5, 1974 | Japan | 49-15282 |
| Feb. 5, 1974 | Japan | 49-15281 |

[52] U.S. Cl. .................... 260/239 BB; 424/244
[51] Int. Cl.² ................................ C07D 225/06
[58] Field of Search ............... 260/239 BB

[56] References Cited
FOREIGN PATENTS OR APPLICATIONS
611,000   5/1962   Belgium ............... 260/239 BB

*Primary Examiner*—Donald G. Daus
*Assistant Examiner*—D. B. Springer

[57] ABSTRACT

Novel 4-Benzazonine derivatives and their salts, and processes for the preparation thereof are disclosed. These 4-benzazonine derivatives are represented by the following general formula:

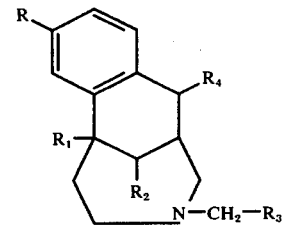

wherein R stands for —H, —OH or a lower alkoxy group such as —OCH$_3$, R$_1$ designates —H or a lower alkyl group such as —CH$_3$ and —CH$_2$CH$_3$, R$_2$ indicates —H or a lower alkyl group such as —CH$_3$, R$_3$ stands for —H, a linear or branched, saturated or unsaturated alkyl group having 1 to 4 carbon atoms, a mono- or di-hydroxy lower alkyl group such as —CH$_2$OH and

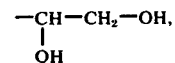

a saturated cyclic hydrocarbon group having 3 to 6 carbon atoms or a substituted or unsubstituted aromatic hydrocarbon group having 6 to 8 carbon atoms, and R$_4$ designates —H, —OH or = O. These compounds have medicinal effects, especially therapeutic activities on the central nervous system, such as analgesic, antitussive and sedative activities.

18 Claims, 6 Drawing Figures

4-BENZAZONINE DERIVATIVES AND PROCESS FOR PREPARATION THEREOF

BACKGROUND OF THE INVENTION

1. Field of the Invention

This invention relates to novel 4-benzazonine derivatives and their salts having therapeutical activities on the central nervous system with low toxicity, and to processes for the preparation of these derivatives and salts.

2. Description of the Prior Art

It is known that 3-benzazonine derivatives which are considered to be compounds having a morphinan structure in which the ring C is cleft have an analgesic activity. Among these derivatives, 1, 2, 3, 4, 5, 6-hexahydro-3-(3-methyl-2-butenyl)-6, 11-dimethyl-8-hydroxy-2, 6-methano-3-benzazonine generally called "pentazocine"; Journal of Medicinal Chemistry, 7, 123 (1964) and Chemical Abstracts, 58, 2440$^b$ (1963) is used for therapeutic purposes. Morphinan and pentazocine have structures represented by the following formulae:

Morphinan

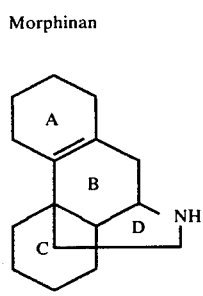

Pentazocine

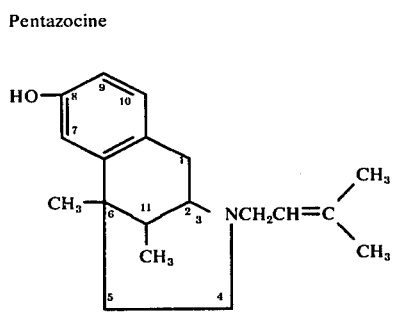

SUMMARY OF THE INVENTION

As a result of our research work, we established processes for the preparation of 4-benzazonine derivatives having a structure in which the ring C of morphinan is cleft or removed, the ring D is a 7-membered ring and the ring B has a hydroxyl group, and we have now arrived at this invention based on the finding that these derivatives have pharmacological activities similar to those of pentazocine.

DETAILED DESCRIPTION OF THE INVENTION

This invention relates to 4-benzazonine derivatives and their pharmacologically active salts, and to processes for the preparation thereof.

4-Benzazonine derivatives of this invention are novel compounds represented by the following general formula (1):

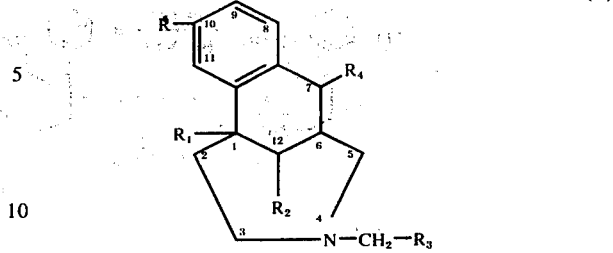

wherein R stands for hydrogen, a hydroxyl group or a lower alkoxy group having 1 to 3 carbon atoms, $R_1$ designates hydrogen or a lower alkyl group having 1 to 3 carbon atoms, $R_2$ indicates hydrogen or a lower alkyl group having 1 to 2 carbon atoms, $R_3$ stands for hydrogen, a linear or branched, saturated or unsaturated alkyl group having 1 to 4 carbon atoms, a mono- or di-hydroxyalkyl group having 1 to 2 carbon atoms, a saturated cyclic hydrocarbon group having 3 to 6 carbon atoms or a substituted or unsubstituted aromatic hydrocarbon group having 6 to 8 carbon atoms, and $R_4$ designates hydrogen, —OH or = O.

This invention relates to novel 4-benzazonine derivatives represented by the above general formula (1) and their salts, and to processes for the preparation thereof.

Starting substances necessary for the synthesis of compounds represented by the general formula (1) can easily be prepared by the methods described in The Journal of Organic Chemistry, 25, 1386 (1960), Journal of Medicinal Chemistry, 13, No. 4, 631 (1970), and Chemical & Pharmaceutical Bulletin, 21, No. 5, 1060 (1973). For instance, starting substances for the synthesis of compounds represented by the following formula

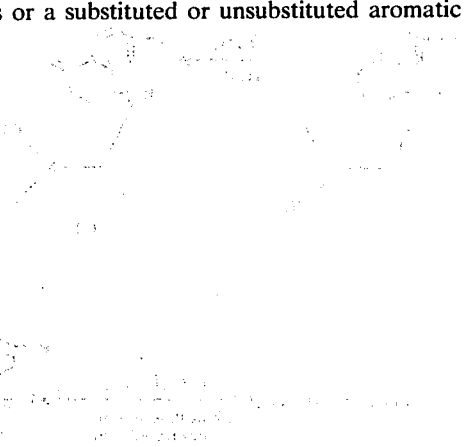

can be prepared through reactions shown by the following reaction formulae:

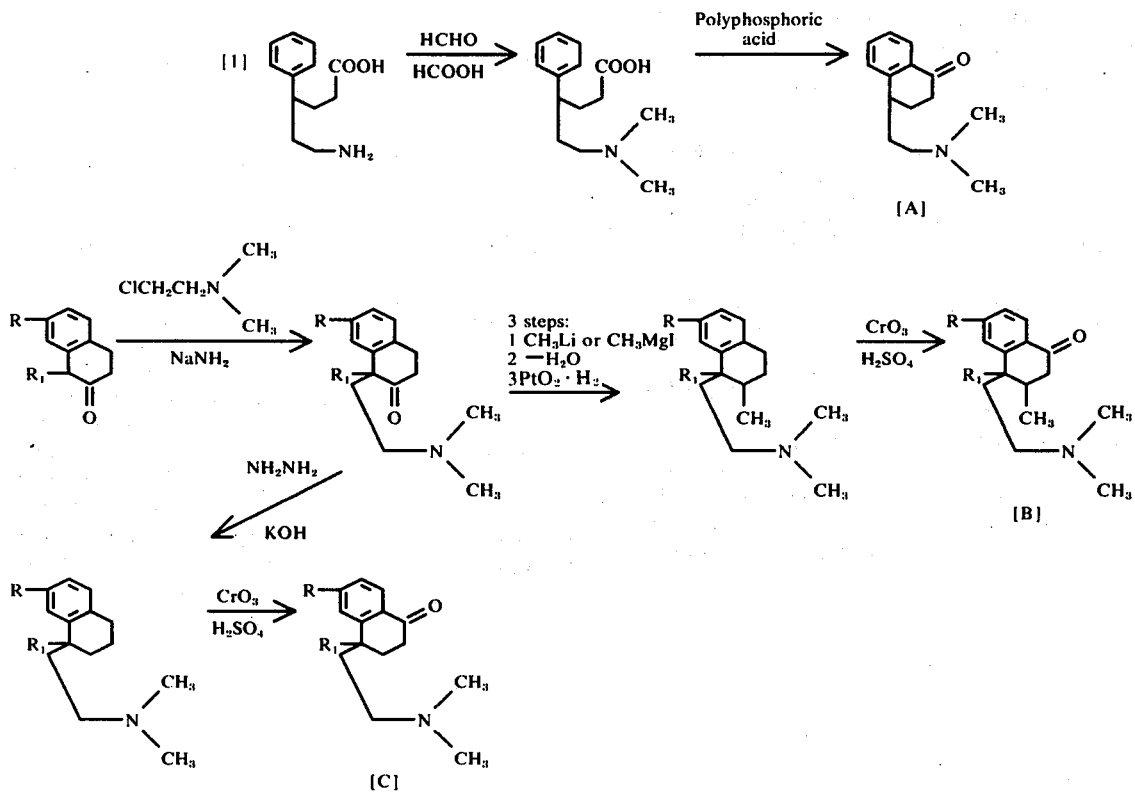

Typical instances of compounds of this invention and of preparation processes will now be described.

1. Process for the preparation of a compound represented by the following formula:

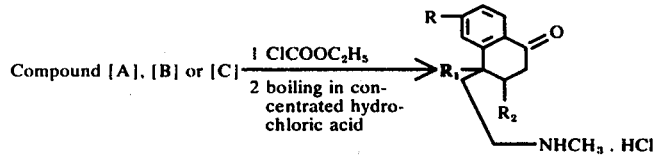

(this compound will hereinafter be referred to as "compound A").

A solvent-soluble salt of an α-tetralone represented by the following general formula:

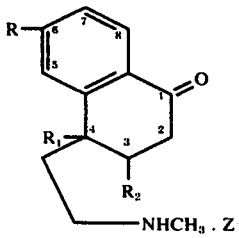

wherein R, $R_1$ and $R_2$ are as defined above, and Z indicates an inorganic acid such as hydrochloric acid or sulfuric acid, such as 4-(N-methylaminoethyl)-3,4-dihydronaphthalen-1(2H)-one, is subjected to the Mannich reaction with formaldehyde, preferably formalin, in the presence of a solvent such as water and a lower alcohol, e.g., methanol, ethanol or propanol, preferably methanol, to thereby effect ring closure and form a 7-membered ring, whereby the compound A, namely a 4-methyl-2,3,4,5-tetrahydro-1,6-methano-1H-4-benzazonin-7(6H)-one derivative, is obtained.

The amount of the solvent used for the Mannich reaction is sufficient if the α-tetralone derivative salt and formaldehyde are completely dissolved in the solvent at room temperature, but it is preferred that the amount of the solvent be 10 to 40 times the amount of the reactants on the weight basis. In order to prevent occurrence of side reactions, it is preferred that the reaction be carried out at a low temperature for a short time. More specifically, it is desired that the reaction be conducted at 20° to 70° C. for 20 to 70 hours. Formaldehyde is used in an amount equivalent to the amount of the α-tetralone derivative or in an excess amount. In general, it is advantageous that the amount of formaldehyde be about 2 to about 10 times the equivalent amount.

2. Process for the preparation of a compound represented by the following formula:

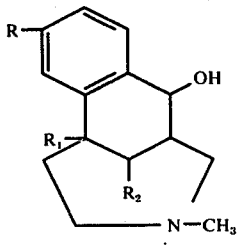

(this compound will hereinafter referred to as "compound B").

A compound B, for example, 4-methyl-2,3,4,5,6,7-hexahydro-1,6-methano-1H-4-benzazonin-7-ol, can be obtained by reducing a compound A, for example, 4-methyl-2,3,4,5-tetrahydro-1,6-methano-1H-4-benzazonin-7(6H)-one.

For accomplishing this reduction, it is preferred to adopt a method using as a reducing agent a complex metal hydride such as LiAlH$_4$ or NaBH$_4$. Use of a solvent is indispensable for this reduction. Anhydrous ether, tetrahydrofuran and dioxane are used when LiAlH$_4$ is employed as the reducing agent, and when NaBH$_4$ is employed as the reducing agent, a lower alcohol, preferably methanol, is used as the solvent. The amount of the solvent used is not a critical factor influencing the progress of the reaction, and the solvent may be used in such an amount as adopted in customary methods. It is preferred that the amount of the solvent be 20 to 30 times the amount of LiAlH$_4$ or NaBH$_4$ on the weight basis.

In the case of LiAlH$_4$, it is preferred that the reduction be carried out at a temperature ranging from 0° C. to the boiling point of the solvent used. The reaction time is varied depending on the boiling point of the solvent used, but in general, the reaction is carried out for 1 to 15 hours. For example, good results can be obtained when the reaction is carried out for 4 to 8 hours by employing dioxane as the solvent.

In case the reduction is performed by employing NaBH$_4$, it is preferred that the reaction be conducted at 10° to 30° C. for 1 to 3 hours, though the reaction can proceed even at −10° C.

The complex metal hydride is used in an amount equivalent to the compound A or in an excess amount, preferably up to 2 to 3 times the equivalent amount.

As another method for the reduction, there can be employed a method in which known reducing agents consisting of a combination of an alkali or alkaline earth metal, preferably sodium, and an alcohol, or known aluminum alcoholates such as aluminum isopropylate are employed. In this method, the reducing agent is used in an amount of 2 to 6 times the equivalent amount according to conventional techniques.

As still another method for the reduction, there can be employed a method in which hydrogenation is performed with use of a known hydrogenation catalyst such as nickel, platinum and palladium catalysts. In this method, the catalyst is used in the finely divided state alone or in the form supported on a carrier such as activated carbon, diatomaceous earth and barium sulfate. The amount used of the catalyst is not critical but can be changed within a broad range. This hydrogenation reaction is conducted under atmospheric pressure or slightly elevated pressure (preferably 1 to 3 atmospheres) under agitation. High reaction temperatures are likely to cause side reactions to occur, and therefore, it is preferred that the reaction be carried out at a temperature ranging from room temperature to about 60° C. It is desired that hydrogen is absorbed in the equivalent amount or an amount slightly excessive over the equivalent amount. Absorption of too excess amount of hydrogen is not preferred because side reactions occur and the yield of the intended product is reduced.

3. Process for the preparation of a compound represented by the following general formula:

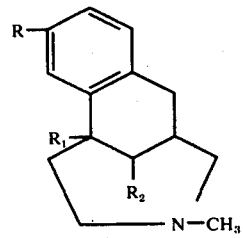

(this compound will hereinafter be referred to as "compound C").

A compound C, for example, 4-methyl-2,3,4,5,6,7-hexahydro-1,6-methano-4-benzazonine, can be prepared by reducing a compound B, for example, 4-methyl-2,3,4,5,6,7-hexahydro-1,6-methano-1H-4-benzazonin-7-ol.

The removal of the OH group at the 7-position can be accomplished by known methods, such as the Clemmensen reduction method, the method using hydrogen activated by a catalyst and the method in which the OH group is first replaced by a halogen, for example, Cl, Br and I, and dehalogenation is then performed with use of a metal such as sodium, zinc, magnesium, iron or tin. Each of these known methods, however, is defective in that the reaction course is long or a long time is required for completion of the reduction. Furthermore, in these known methods, the isolation of the intended product from the reaction mixture liquid, which is conducted after completion of the reaction, involves complicated operations.

In the synthesis of the compound C, it has been found that the reduction is performed with use of hydriodic acid and red phosphorus. The object can be attained when hydriodic acid and red phosphorus are used in equivalent amounts, but it is preferred that they be used in slight excess amounts. In general, it is desired that hydriodic acid be used in an amount of 2 to 4 moles per mole of the compound B and red phosphorus be used in an amount of 1 to 2 atoms per mole of the compound B.

The concentration of hydriodic acid has influence on the reaction rate and the yield of the intended product, and when the concentration of hydriodic acid is lower than 10%, the reaction time is much prolonged. It is preferred that the concentration of hydriodic acid be within a range of 20 to 57% (the concentration of hydriodic acid for industrial use). The reaction is carried out at 60° to 160° C. under atmospheric or elevated pressure. It is preferred that the reaction be conducted at 100° to 120° C. under atmospheric pressure, and in this case the reaction is completed in from about 1 to about 6 hours.

It has been found that when the reaction is carried out in the presence of a solvent including acetic acid and further apply the compound B in which R stands for —OH or —OCH$_3$, the yield of the intended compound C can be increased. It is desired that acetic acid be used in an amount of 1 to 10 moles per mole of the compound B. It is not advantageous to use too little or too great an amount of acetic acid.

4-I process for the preparation of a compound represented by the following general formula:

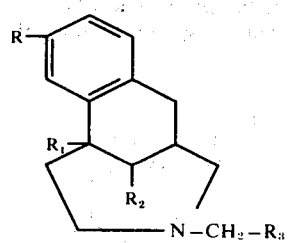

(this compound will hereinafter be referred to as "compound D").

The compound D can be prepared by reacting a 4-benzazonine derivative represented by the following formula:

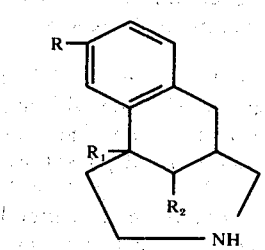

(this compound will hereinafter be referred to as "starting compound K") with a compound represented by the general formula X—CH$_2$—R$_3$ in which X stands for a halogen atom, an alkyl-SO$_2$O— or aryl-SO$_2$—O— group and R$_3$ is as defined above [method (a)], by reacting the starting compound K with a compound represented by the general formula

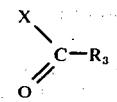

in which X and R$_3$ are as defined above, and reducing the resulting reaction product with a complex metal hydride [method (b)], and by reacting the starting compound K with a compound represented by the general formula

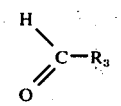

in which R$_3$ is as defined above, in the presence of formic acid or hydrogen activated by a catalyst [method (c)].

The starting compound K to be used in the foregoing methods (a), (b) and (c) can be prepared, for example, according to the reaction represented by the following reaction formula:

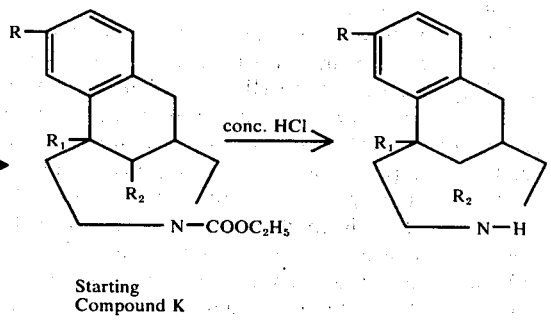

Starting Compound K

The above methods (a), (b) and (c) will be described below.

Method (a)

The starting compound K is reacted with an alkylating agent of the formula X—CH$_2$—R$_3$ in the equivalent amount or in an amount slightly excessive over the equivalent amount in the presence of an appropriate acid binder. As the acid binder, there are employed amines such as triethylamine, dicyclohexylethylamine or the like, and sodium carbonate, potassium carbonate, sodium bicarbonate or the like. It is preferred that the amount of the acid binder used be 1.5 to 2 times the equivalent amount.

This reaction is preferably accomplished in the presence of a solvent such as ether, tetrahydrofuran, dioxane, dimethylformamide, chloroform, benzene, toluene, alcohol or a mixture of two or more of these solvents. The amount used of the solvent is not particularly critical, but it is desired that the solvent be used in an amount 1 to 10 times the total amount of the reactants used on the weight basis.

The reaction temperature can be changed within a broad range. For instance, it is preferred that the reaction be carried out at a temperature ranging from 0° C. to the boiling point of the solvent used.

The reaction is completed within 0.5 to 5 hours, but in case a lower alkyl chloride or bromide is used, it is preferred that the reactants be heated at 50° to 100° C. in a sealed tube under shaking for 1 to 10 hours. Use of a lower alkyl iodide is advantageous, because the reaction is accomplished by conducting heating underreflux at atmospheric pressure.

Method (b)

The starting compound K is reacted with a carboxylic acid halide represented by the formula

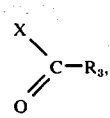

preferably a carboxylic acid chloride, in the presence of a dehydrohalogenation agent to form a 4-acyl compound represented by the following general formula:

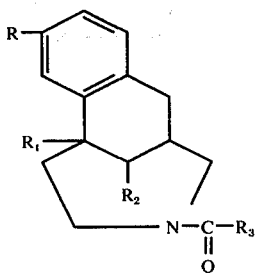

wherein R, $R_1$, $R_2$ and $R_3$ are as defined above, and then, the so formed 4-acyl compound is reduced with a complex metal hydride such as lithium aluminum hydride or di-isobutyl aluminum hydride to form a compound D.

The 4-acyl compound of the above general formula is synthesized according to the Schotten-Baumann process. It is desired that this reaction be carried out in the presence of a dehydrohalogenation agent such as an organic amine, e.g., triethylamine, dicyclohexylethylamine or the like by employing a solvent such as ether, benzene, toluene or chloroform.

In the subsequent reduction, it is preferred that lithium aluminum hydride be used as the complex metal hydride. The complex metal hydride is used in the equivalent amount of preferably in an excess amount, namely in an amount up to 4 times the equivalent amount.

This reduction reaction is carried out in such a solvent as ether, tetrahydrofuran, dioxane or the like. It is preferred that the solvent be used in such an amount that the 4-acyl compound is completely dissolved at the reaction temperature.

The reaction temperature is adjusted within a range of from 0° C. to the boiling point of the solvent used.

The reaction time is varied depending on the reaction temperature, but in general, the reaction is completed within about 12 hours.

Method (c)

The reaction between the starting compound K and an aldehyde of the general formula

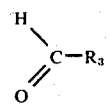

is the presence of formic acid proceeds in an aqueous solution or in the absence of a solvent. In the case of acetaldehyde or propylaldehyde, it is preferred that the reaction be conducted in an aqueous solution, and in the case of other aldehydes it is preferred that the reaction be carried out in the absence of a solvent. The aldehyde is used in the equivalent amount or an excess amount. It is desired that the aldehyde be used in an excessive amount of up to 3 moles per mole of the starting compound K. Formic acid is used in an excess amount, preferably up to 10 moles per mole of the starting compound K. The reaction temperature is 50° to 200° C., preferably 80° to 150° C. It is desired that the heating be conducted for 1 to 4 hours.

As a modification of this method, there is mentioned a reductive alkylation method using catalytically activated hydrogen. The aldehyde is used in the equivalent amount or in an excess amount preferably in an excess amount of up to 2 moles per mole of the starting compound K. This reaction is carried out in the presence of an appropriate solvent, for example, alcohols, preferably methanol or ethanol. It is advantageous to use the catalysts such as Raney nickel, palladium and platinum. It is preferred that palladium and platinum be used in the state dispersed on a carrier such as active carbon and diatomaceous earth. In this case, the preferred catalyst content is within a range of from 5 to 10%, though the amount of the catalyst is not particularly critical. The hydrogenation is conducted under atmospheric pressure or slightly elevated pressure, preferably 1 to 3 atmospheres, under agitation. Since a high temperature causes side reactions, it is preferred that the hydrogenation be conducted at a temperature ranging from room temperature to 60° C. It is desired that the reaction be conducted so that the amount absorbed of hydrogen approximates the equivalent amount. 4-II Another process for the preparation of the Compound D.

When a compound represented by the following formula:

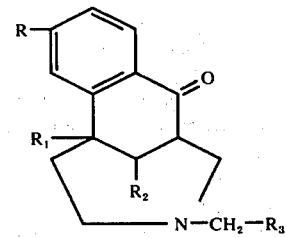

is reduced with active hydrogen, the compound D can be obtained.

This process is substantially accomplished in one step, and the compound D can be prepared in a short time. Accordingly, this process is advantageous from the industrial viewpoint.

Various catalysts can be used for activation of hydrogen, and a palladium catalyst is most preferred among them. The palladium catalyst is used in the finely dispersed state alone or in the form supported on a carrier such as activated carbon, barium sulfate or the like.

The amount of the catalyst is not particularly critical but can be varied within a broad range.

A polar solvent such as acetic acid, ethanol or methanol is preferably used as the reaction solvent. It is suitable to use the solvent in an amount 3 to 100 times the amount of the compound to be reduced on the weight basis.

The hydrogenation is accomplished by introducing hydrogen into the reaction mixture under shaking or agitation at atmospheric pressure.

It is preferred that the reaction be conducted at a temperature ranging from room temperature to the boiling point of the solvent used. It is permissible to conduct the heating in two stages, if necessary.

The reduction proceeds substantially in the following manner:

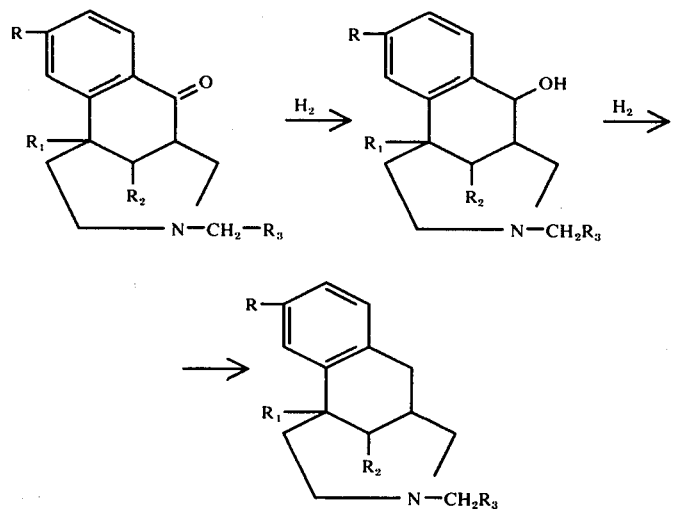

When the reaction is conducted at room temperature, an intermediate 7-hydroxy compound is mainly formed. If the intermediate is further reduced at a temperature not lower than 50° C., the intended compound D can be obtained. Thus, the process 4-II of this invention includes an embodiment where the compound D is formed through an intermediate.

The reaction time can be changed within a broad range depending on the reaction conditions, and a reaction time of 5 to 10 hours is sufficient.

It has been found that addition of a strong acid such as hydrochloric acid, perchloric acid or sulfuric acid accelerates this reaction and results in increase of the intended compound D. It is preferred that such strong acid be added in an amount of 1 to 5 moles per mole of the compound to be reduced.

The reaction is carried out at a pressure ranging from atmospheric pressure to about 10 atmospheres. Though the reaction pressure has no substantial influence on the reaction rate or the yield of the intended compound D, it is preferred that the reaction be conducted at atmospheric pressure.

5-I Process for the preparation of a compound represented by the following formula:

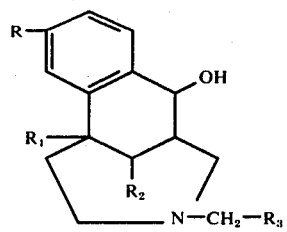

(this compound will hereinafter be referred to as "compound E").

A 4-benzazonine derivative represented by the following general formula:

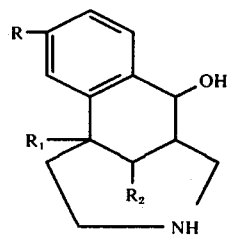

(this compound will hereinafter be referred to as "starting compound L") is converted to the compound E by reacting the starting compound L with a compound represented by the general formula X—CH$_2$—R$_3$ in which X and R$_3$ are as defined above [method (a)] or by reacting the starting compound L with a compound represented by the general formula

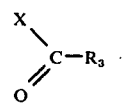

in which X and R$_3$ are as defined above and reducing the resulting reaction product with a complex metal hydride [method (b)]. Conditions adopted in these methods (a) and (b) are substantially identical with those adopted in methods (a) and (b) of the process 4-I. The starting compound L is prepared, for example, in the following manner:

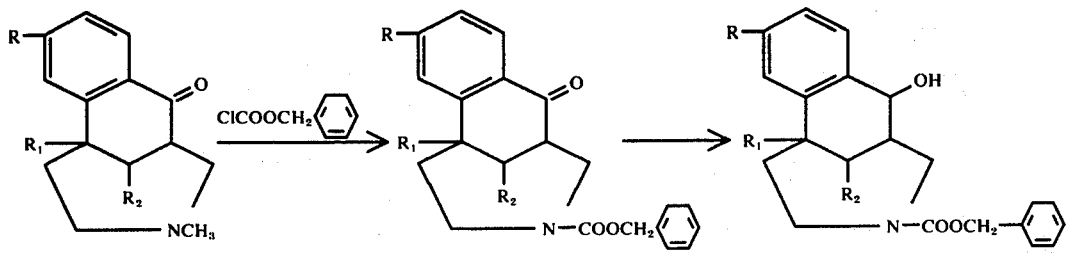

Compound A

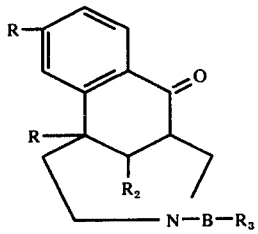

Starting Compound L

5-II Another process for the preparation of a compound E.

A compound E can be prepared by reducing a compound represented by the following general formula (hereinafter referred to as "compound F"):

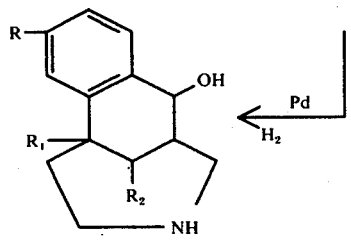

wherein B stands for —CO— or —CH$_2$—.

The reduction of the compound F is preferably accomplished by a method using as a reducing agent a complex metal hydride such as lithium aluminum hydride and sodium boron hydride or by a method in which hydrogenation is conducted with use of such a catalyst as platinum or palladium.

The complex metal hydride is used in an amount slightly in excess of the equivalent amount in the compound F, preferably 1.5 to 4 times the equivalent amount. This reduction is conducted in an appropriate solvent. For instance, ether, tetrahydrofuran, dioxane or the like is used in the case of lithium aluminum hydride, and methanol, ethanol or the like is used in the case of sodium boron hydride.

The amount used of the solvent is not particularly critical, but it is necessary that the solvent be used at least in such an amount as to completely dissolve the compound F at the reaction temperature.

The reaction temperature can optionally be chosen within a range of −10° C. to the boiling point of the solvent used.

The reaction time is varied depending on the reaction temperature, and in general, the reaction is completed within 24 hours.

In the case of the hydrogenation reduction using platinum, palladium or the like as a catalyst, the hydrogenation catalyst is used in the finely dispersed state alone or in the form supported on a carrier such as activated carbon and barium sulfate. The amount of the catalyst used is not particularly critical but can be varied within a broad range.

Acetic acid, ethanol or methanol is preferably used as a solvent, and it is preferred that the solvent be used in an amount 30 to 100 times the amount of the compound to be reduced on the weight basis.

The reduction is accomplished by introducing hydrogen gas into the reaction mixture under shaking or agitation at atmospheric or elevated pressure. The reaction proceeds relatively smoothly at atmospheric pressure and room temperature. It is preferred that hydrogen be absorbed in an amount slightly greater than the calculated equivalent amount.

It has been found that when this reaction is conducted under high temperature and high pressure conditions, side reactions are caused to occur and the yield of the intended product is reduced. It has also been found that the reaction is accelerated if such a compound as hydrochloric acid or perchloric acid is present in the solvent.

The compound F can be prepared by applying the above-mentioned method 4-I (a) or 4-I (b) to a compound represented by the following general formula:

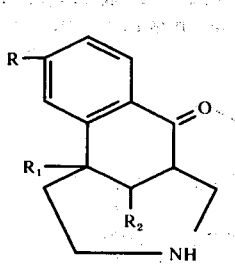

(this compound will hereinafter be referred to as "starting compound M").

This compound M can be prepared, for example, in the following manner:

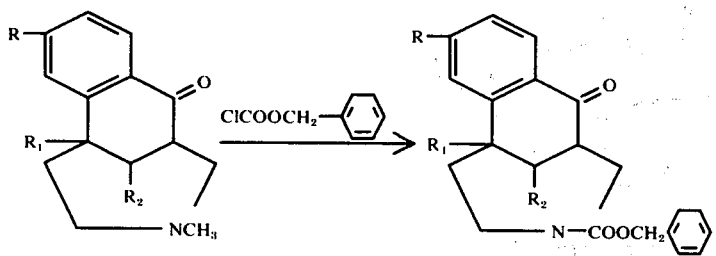

Compound A

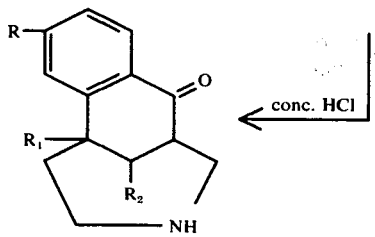

6. Process for the preparation of a compound represented by the following general formula:

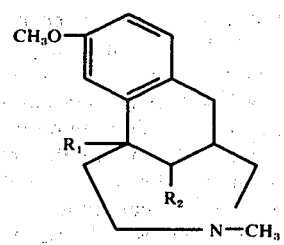

(this compound will hereinafter be referred to as "compound G").

This compound E can be prepared by methoxylating a compound represented by the following general formula:

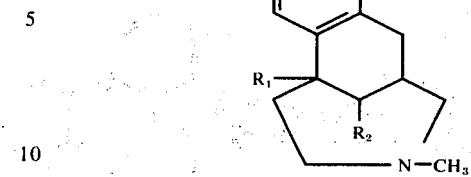

(this compound will hereinafter be referred to as "compound C'").

The methoxylation of the hydroxyl group at the 10-position, namely the phenolic hydroxyl group, is generally performed with use of dimethyl sulfate or methyl p-toluenesulfonate. However, in this case, side reactions readily occur and the yield of the intended compound is reduced.

If the methoxylation is carried out with use of diazomethane or trimethylphenyl ammonium hydroxide, the intended product can be obtained in a high yield in the pure form.

In case diazomethane is used for the methoxylation, the object can be attained if it is used in an amount equivalent to the compound C', namely 1 mole per mole of the compound C', but it is preferred that diazomethane be used in an excess amount of up to about 2 moles per mole of the compound C'.

The presence of a solvent is not indispensable, but in the case of diazomethane, in view of the handling it is preferred that ether or chloroform be used as a solvent. The advance of the reaction is not influenced by the amount of the solvent used.

Preferred reaction temperatures are within a range of from $-10°$ to $10°$ C. The reaction is completed within about 1 to about 10 hours, and during the reaction there is observed generation of nitrogen gas. Since diazomethane is a very poisonous gaseous compound, it is desired that the resulting product mixture be treated after it has been allowed to stand still for 10 to 20 hours for complete decomposition of diazomethane.

As pointed out above, diazomethane is a poisonous gaseous substance. It is also explosive. Therefore, it is possible to adopt a method in which a diazomethane-forming compound such as nitrosomethyl urea, nitrosomethyl urethane or N-nitroso-β-methylamino-isobutyl methylketone is present in ether or a lower alcohol, preferably ether or methanol, and the reaction is conducted while generating diazomethane by adding sodium hydroxide, potassium hydroxide or sodium alcoholate to the mixture. In this case, it is preferred that the reaction be carried out at −10° to 10° C.

In case the methoxylation is performed with use of trimethylphenyl ammonium hydroxide, the heating is conducted in the absence or presence of a solvent by employing trimethylphenyl ammonium hydroxide in an amount of 1 to 2 moles per mole of the compound C'. A method in which dimethylaniline formed as a by-product is removed by steam distillation is preferably adopted.

This reaction is allowed to proceed at temperatures ranging from about 60° to about 200° C., and the reaction time is generally within a range of 30 minutes to 2 hours. It is preferred that the reaction is carried out at a temperature of about 100° to about 110° C. for 1 to 4 hours.

In a modification of this process, the trimethylphenyl ammonium hydroxide is used in the following manner. More specifically, sodium hydroxide, potassium hydroxide or an alkali metal alcoholate is added to a methanol or ethanol solution of a trimethylphenyl quaternary ammonium salt (inclusive of halides and p-toluenesulfonates), the precipitated sodium or potassium salt is removed by filtration, and the methanol or ethanol solution of trimethylphenyl ammonium hydroxide obtained as the filtrate is used directly for the reaction.

The compound C' can be prepared, for example, in the following manner:

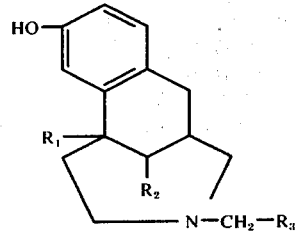

(this compound will hereinafter be referred to as "compound H").

This compound H can be prepared by reacting a compound represented by the following general formula:

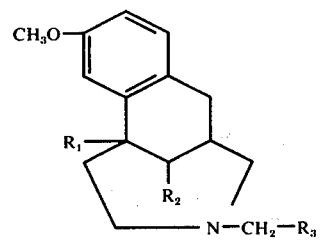

(this compound will hereinafter be referred to as "compound I") with a mineral acid, for example, hydrobromic acid, hydriodic acid or sulfuric acid.

As the mineral acid, there are preferably employed hydrohalogenic acids, and use of hydrobromic acid is most preferred because the resulting 4-benzazonine derivative is readily crystallized in the form of a hydrobromide.

In this reaction, the amount of the acid used, the

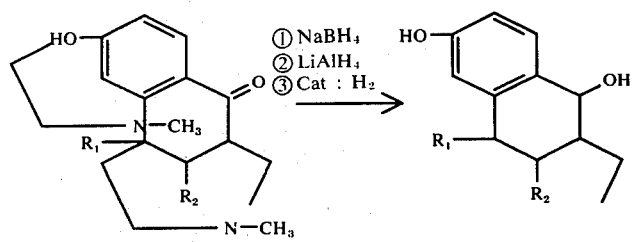

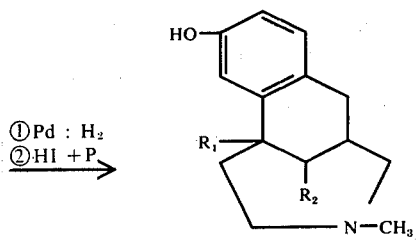

7. Process for the preparation of a compound represented by the following general formula:

reaction time and the heating time are not particularly critical, but in general, it is preferred that the reaction be conducted under reflux for 30 minutes to 1 hour by employing the acid in an amount 5 to 10 times the amount of the compound I. It is desired that the reaction mixture be heated so that it is kept refluxed. However, if the —CH$_2$—R$_3$ of the compound I is an unstable group such as a cyclopropylmethyl or a cyclobutyl methyl group, it is preferred that the amount used of the acid be relatively lowered and the heat refluxing be conducted under mild conditions for a short time.

The compound I used as the starting compound in this process is included in the scope of the intended product of this invention, and it can be prepared, for example, by the process 4-I.

8. Process for the preparation of a compound represented by the following general formula:

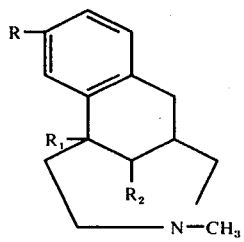

(this compound will hereinafter be referred to as "compound J").

This compound J can be prepared by reducing a compound A with activated hydrogen.

As regards the reduction of the $>C=O$ group at the 7-position to a $>CH_2$ group, there is known a two-stage method comprising reducing the $>C=O$ group with, for example, a complex metal hydride to convert it to a $>CH-OH$ group and further reducing it with hydriodic acid and red phosphorus. This method, however, is defective in that the reaction course is very long and complicated operations are included.

In the process of this invention, activated hydrogen is used for the reduction. Known catalysts for the catalytic reduction can be used for activation of hydrogen, and palladium is most preferred among them. The catalyst is used in the finely dispersed state alone or in the form supported on a carrier such as activated carbon or barium sulfate. The amount of the catalyst used is not particularly critical but can be changed within a broad range. Polar solvents such as acetic acid, ethanol and methanol are preferably employed as the reaction solvent, and it is preferred that the solvent be used in an amount 30 to 100 times the amount of the substance to be reduced on the weight basis. The catalytic hydrogenation is performed by introducing hydrogen gas into the reaction mixture under shaking or agitation at atmospheric or elevated pressure. It is preferred that the reaction is carried out at a temperature ranging from about 50° C. to the boiling point of the solvent used. The reaction time is varied depending on the reaction temperature and the degree of contact between the reaction solvent and hydrogen gas, namely the degree of shaking or agitation, but it is sufficient if the reaction is conducted for about 5 to about 10 hours.

It has been found that this reaction can be accelerated and the yield of the intended compound J can be increased, if a small amount of such a compound as hydrochloric acid or perchloric acid is added. It is preferred that such compound be added in an amount of 1 to 5 moles per mole of the compound to be reduced.

The reaction pressure has no substantial influence on the reaction rate or the yield of the intended compound, but it is preferred that the reaction be carried out at a pressure of up to about 10 atmospheres.

The fact that compounds of this invention represented by the following general formula:

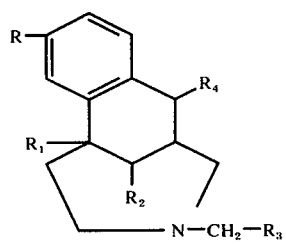

are 4-benzazonine derivatives having a "7-membered ring" has been confirmed by the following tests.

For example, when 4-(N-methylaminoethyl)-3,4-dihydronaphthalen-1(2H)-one hydrochloride or 6-methoxy-4-methyl-4-(N-methylaminoethyl)-3,4-dihydronaphthalen-1(2H)-one hydrochloride was reacted with formaldehyde, the product was converted to a picrate and was purified and subjected to elementary analysis, there was indicated a composition represented by the formula $C_{14}H_{17}ON$ or $C_{16}H_{21}O_2N$.

Further, in IR spectra (see FIGS. 1 and 2) and NMR spectra (see FIGS. 3 and 4) of the above compounds, no absorption inherent of the $>NH$ group was present and from these spectra, it was confirmed that the above compounds have $>C=O$ and $>NCH_3$ groups.

Compounds of this invention represented by the above general formula are generally insoluble in water, but they are readily rendered water-soluble merely by converting them to acid salts according to customary procedures. Either inorganic acids, or organic acids can be used for this purpose. As the inorganic acid, there can be mentioned, for example, hydrochloric acid, hydrobromic acid, sulfuric acid and phosphoric acid, and as the organic acid, there can be mentioned, for example, maleic acid, citric acid, butyric acid and methanesulfonic acid.

Compounds of this invention represented by the above general formula are of low toxicity as compared with known compounds and have therapeutic activities on the central nervous system. They are very valuable as analgesics, antitussives and sedatives. Further, various compounds having similar activities can be derived from the compounds of this invention.

Results of comparative tests where the medicinal effects of compounds of this invention were compared with those of known compounds such as pentazocine and codeine phosphate by employing mice and guinea pigs as the test animals are shown in the following Tables I and II.

Table I

Compounds of Formula

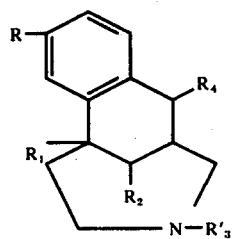

| R | $R_1$ | $R_2$ | $R'_3$ (—$CH_2$—$R_3$) | $R_4$ | Chemical Stimulus Method[1] (Writhing Method) (interabdominal injection) | Heat Stimulus Method[2] (Hot Plate Method) (hypodermic injection) |
|---|---|---|---|---|---|---|
| H | H | H | $CH_2CH=CH_2$ | OH | 1.2 | 1.4 |
| H | H | H | $CH_2CH=C\begin{smallmatrix}CH_3\\CH_3\end{smallmatrix}$ | OH | 1.2 | 1.2 |
| H | H | H | $CH_2CH_2$–⟨phenyl⟩ | OH | 1.8 | 4.5 |
| H | $CH_3$ | H | $CH_3$ | OH | 0.7 | 1.4 |
| H | $CH_3$ | H | $CH_2CH=CH_2$ | OH | 1.8 | 1.5 |
| H | $CH_3$ | H | $CH_2CH=C\begin{smallmatrix}CH_3\\CH_3\end{smallmatrix}$ | OH | 1.5 | 1.5 |
| $CH_3O$ | $CH_3$ | H | $CH_3$ | OH | 1.5 | 5.0 |
| $CH_3O$ | $CH_3$ | H | $CH_2CH=CH_2$ | OH | 1.4 | 1.6 |

| Compounds of Formula R | Pressure Stimulus Method[3] (hypodermic injection) | Acute Toxicity $LD_{50}$, mg/Kg (mouse, intravenous injection) | Remarks |
|---|---|---|---|
| H | 1.4 | 58.0 | |
| H | 1.4 | 60.0 | |
| H | 2.0 | 45.0 | |
| H | 1.2 | 70.0 | |
| H | 2.0 | 55.0 | |
| H | 1.6 | 25.0 | |
| $CH_3O$ | 1.2 | 72.0 | |
| $CH_3O$ | | 61.0 | |

| R | $R_1$ | $R_2$ | $R'_3$ | $R_4$ | 1) | 2) |
|---|---|---|---|---|---|---|
| $CH_3O$ | $CH_3$ | H | $CH_2CH_2$–⟨phenyl⟩ | OH | 1.6 | 2.2 |
| H | $CH_3$ | $CH_3$ | $CH_3$ | OH | 1.6 | 2.0 |
| H | H | H | $CH_2CH=CH_2$ | H | 1.4 | 5.0 |
| H | H | H | $CH_2CH=C\begin{smallmatrix}CH_3\\CH_3\end{smallmatrix}$ | H | 1.0 | 1.5 |
| H | H | H | $CH_2CH_2$–⟨phenyl⟩ | H | 0.8 | 5.0 |
| $CH_3O$ | $CH_3$ | H | $CH_3$ | H | 0.8 | 2.0 |
| HO | $CH_3$ | H | $CH_3$ | H | 1.5 | 2.0 |
| H | H | H | $CH_3$ | H | 2.5 | 0.6 |
| H | H | H | $CH_2$–⟨phenyl⟩ | H | 1.0 | 3.0 |
| HO | $CH_3$ | H | $CH_2CH_3$ | H | 1.5 | 2.0 |
| $CH_3O$ | $CH_3$ | H | $CH_2CH_3$ | H | 0.8 | 2.0 |
| $CH_3O$ | $CH_3$ | $CH_3$ | $CH_2CH_3$ | H | 0.8 | 2.0 |
| HO | $CH_3$ | H | $CH_2CH=C\begin{smallmatrix}CH_3\\CH_3\end{smallmatrix}$ | H | 1.0 | 1.5 |
| $CH_3O$ | $CH_3$ | H | $CH_2CH_2$–⟨phenyl⟩ | H | 1.5 | 2.0 |
| HO | $CH_3$ | H | $CH_2CH_2CH\begin{smallmatrix}CH_3\\CH_3\end{smallmatrix}$ | H | 1.0 | 1.5 |
| pentazocine | | | | | | |

Compounds of Formula  3)  Acute Toxicity  Remarks

Table I-continued

| R | | |
|---|---|---|
| CH₃O | 1.8 | 45.0 |
| H/ 1.5 | 30.0 | trans-form |
| H/ 1.5 | 45.0 | |
| H/ 1.4 | 65.0 | |
| H | 2.0 | 35.0 |
| CH₃O | | 120.0 |
| HO | | 75.0 |
| H | 20.0 | |
| H | | 120.0 |
| HO | | 80.0 |
| CH₃O | | 120.0 |
| CH₃O | | 100.0 trans-form |
| HO | | 40.0 |
| CH₃ | | 48.0 |
| HO | | 40.0 |
| pentazocine | 1.0 | 25.0 |

Notes:
Tested Animal: mice of the ddN-series, . 20 ± 1 experimental Conditions: temperature of 24 ± 1° C., relative humidity of 65 ± 3 %
[1] R. Koster, M. Anderson and E. J. De Beer, Federation Proceedings, 18, 412 (1959)
[2] G. Woolfe and A. D. Mac Donald; Journal of Pharmacology and Experimental Therapeutics, 80, 300 (1944)
[3] A. F. Green, P. A. Yound and E. I. Godfrey; British Journal of Pharmacology and Chemotherapy, 6, 572 (1951)

Table II

Compounds of the formula

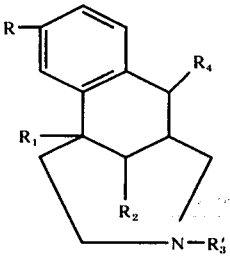

| | | | | | Comparison of Antitusive Effects | | | |
|---|---|---|---|---|---|---|---|---|
| | | | | | Mechanical Stimulus Method[1] | | Chemical Stimulus Method[2] | |
| R | $R_1$ | $R_2$ | $R_3$ ($-CH_2-R_3$) | $R_4$ | $ED_{50}$, mg/Kg | Effect Ratio to Codeine Phosphate | $ED_{50}$, mg/Kg | Effect Ratio to Codeine Phosphate |
| CH₃O— | —CH₃ | —H | —CH₃ | —OH | 13.72 | 105.5 | 6.06 | 218.8 |
| —H | —CH₃ | —H | —CH₃ | —OH | 4.42 | 326.9 | 1.64 | 800.7 |
| —H | —H | —H | —CH₂—CH=CH₂ | —H | 7.42 | 195.0 | 12.67 | 104.7 |
| —H | —H | —H | —CH₃ | —OH | 9.21 | 157.1 | 6.58 | 201.4 |
| —H | —H | —H | —CH₂—CH=CH₂ | —OH | 18.90 | 76.6 | 15.30 | 86.7 |
| codeine phosphate | | | | | 14.47 | 100 | 13.26 | 100 |
| dihydrocodeine phosphate | | | | | 4.65 | 310.7 | 2.65 | 500.4 |

Notes:
1) Takagi et al modification [Journal of the Pharmaceutical Society of Japan, 80, 1497 (1960)] of the test method of H. Konzett and E. Rothlin [Experientia, 10, 472 (1954)], in which urethane was hypodermically injected (15 mg/Kg) into guinea pigs and swine hairs were inserted into the trachea to impart stimulus.
2) Takagi et al modification [Journal of Pharmaceutical Society of Japan, 80, 1497 (1960)] of the test method of H. Friebel, C. Reichle and A. V. Gravenitz [Archiv Fur experimentalle Phathologie und Pharmakologie, Naunyn-Schmiede-berg's, 224,384 (1955)], in which the test compound was hypodermically injected into guinea pigs, 30 minutes after the injection the quinea pigs were put into a desiccator filled with SO₂ gas and kept in the desiccator for 1 minute, then the guinea pigs were put into another vessel and the degree of coughing was examined.

Compounds of this invention represented by the above general formula (1) can be administered orally, intestinally or non-orally according to customary procedures. The compounds of this invention can be formed into preparations suitable for administration, such as tablets, capsules, suppositories, liquid preparations (inclusive of injections), powders or the like, according to customary methods.

DESCRIPTION OF THE PREFERRED EMBODIMENTS

PROCESS FOR SYNTHESIS OF COMPOUND A

Example 1

Figure 1:
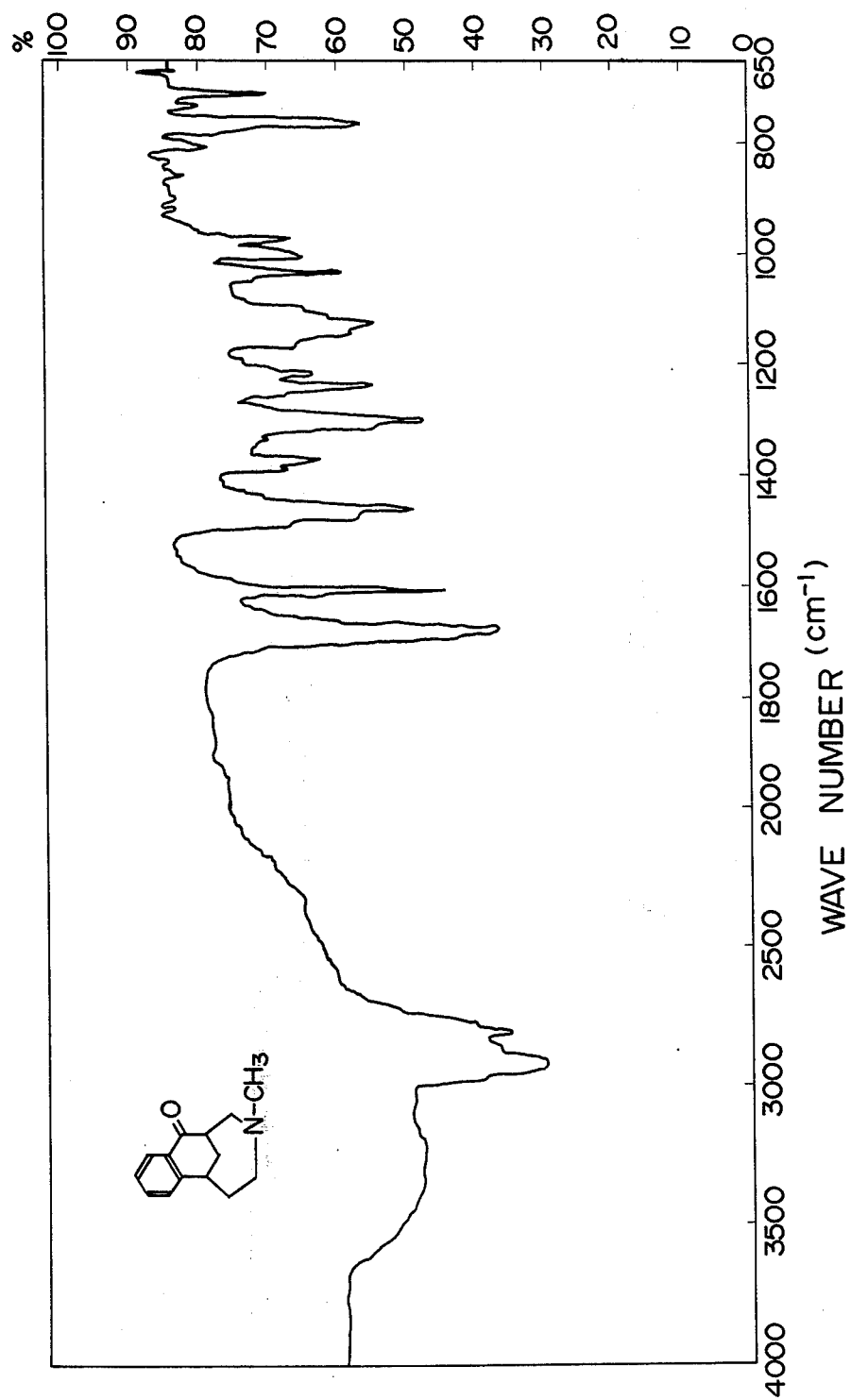
FIG. 1 is an IR spectrum (liquid film method) of 4-methyl-2,3,4,5-tetrahydro-1,6-methano-1H-4-benzazonin-7(6H)-one.
Figure 2:
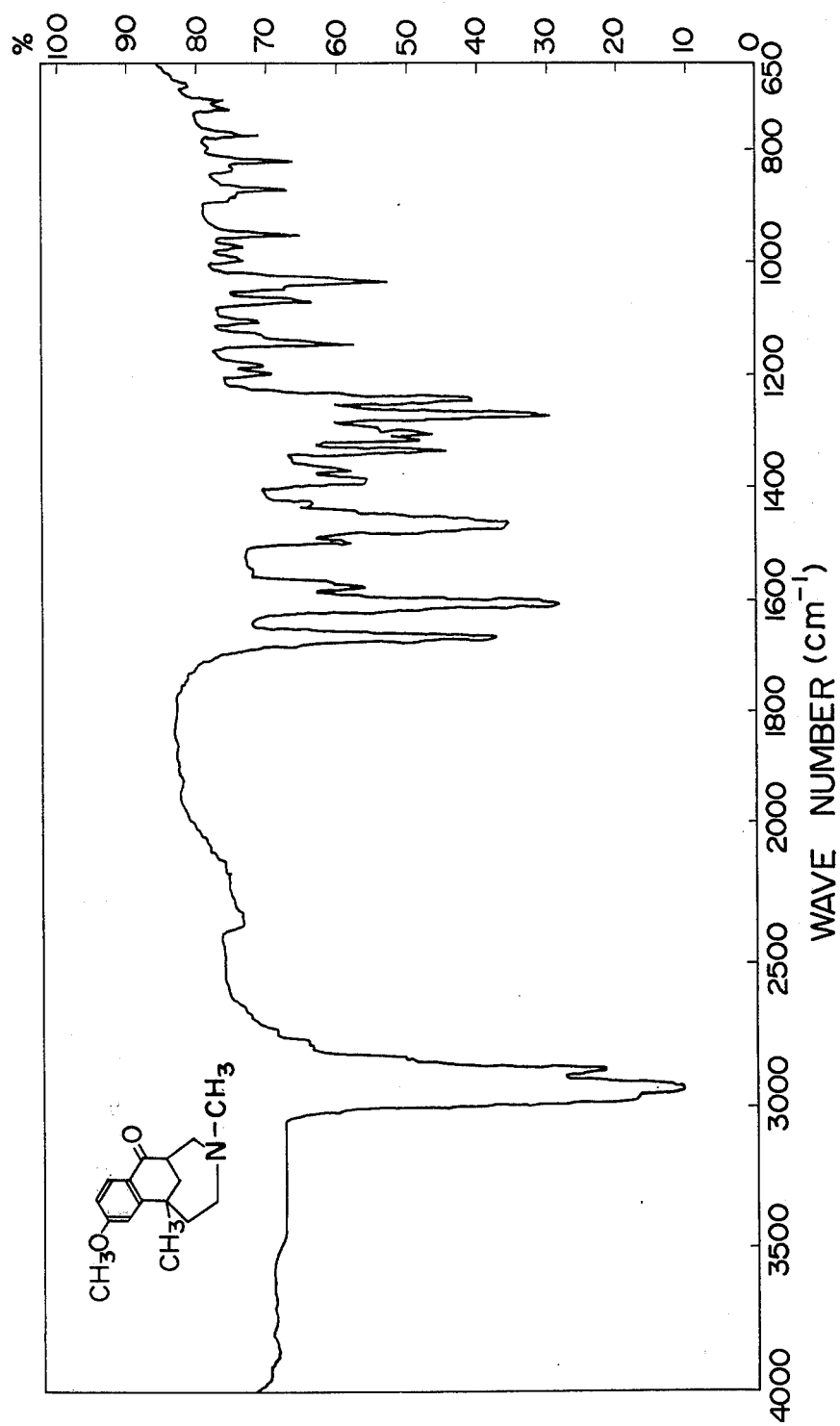
FIG. 2 is an IR spectrum (paste method) of 1,4-dimethyl-10-methoxy-2,3,4,5-tetrahydro-1,6-methano-1H-4-benzazonin-7(6H)-one.
Figure 3:
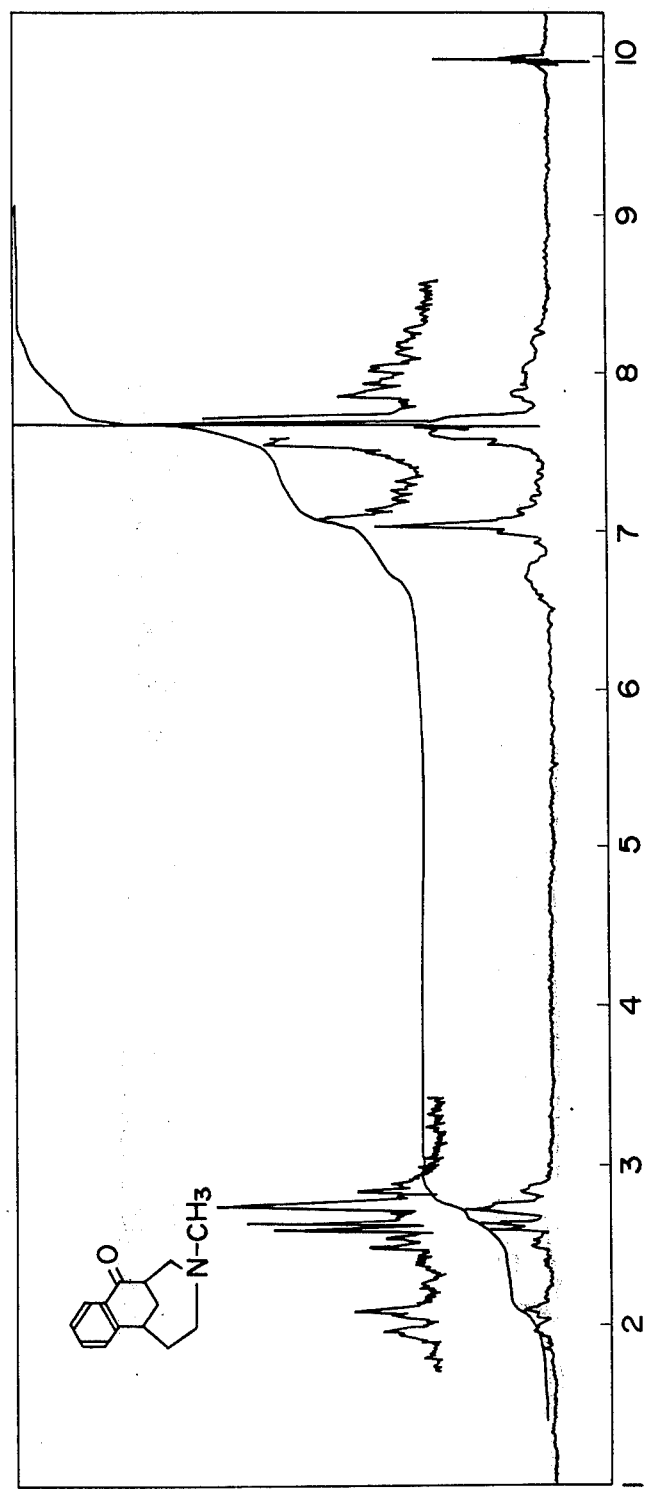
FIG. 3 is an NMR spectrum (CDCl₃ solvent) of 4-methyl-2,3,4,5-tetrahydro-1,6-methano-1H-4-benzazonin-7(6H)-one.
Figure 4:
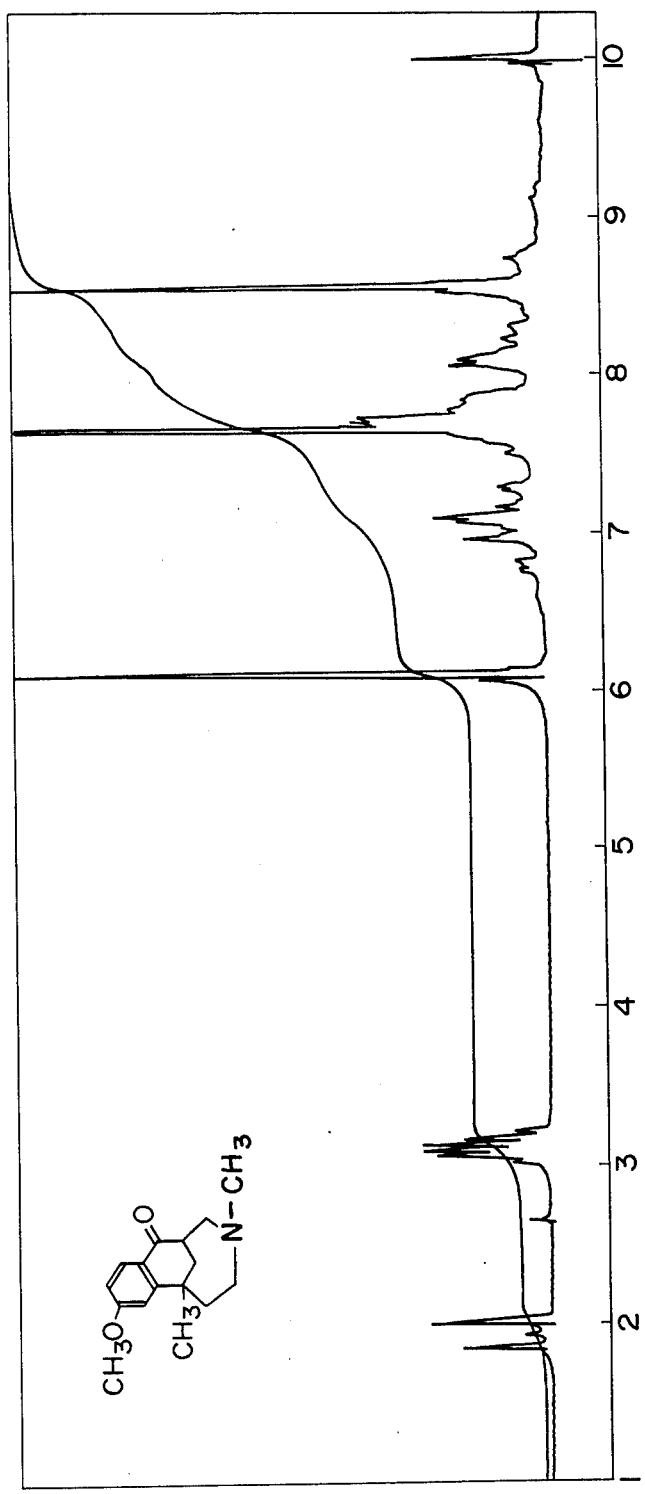
FIG. 4 is an NMR spectrum (CDCl₃ solvent) of 1,4-dimethyl-10-methoxy-2,3,4,5-tetrahydro-1,6-methano-1H-4-benzazonin-7(6H)-one.
Figure 5:
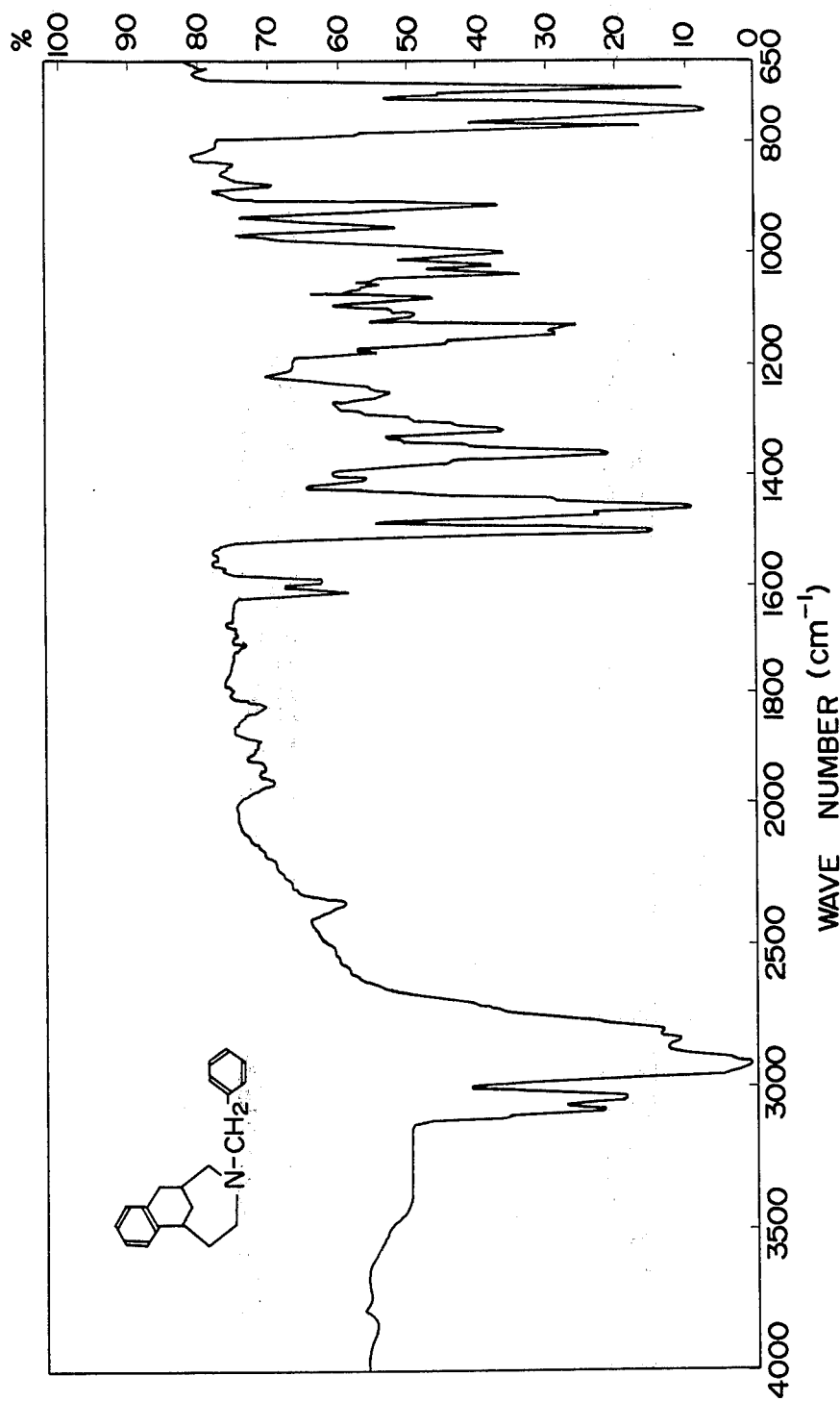
FIG. 5 is an IR spectrum (paste method) of 4-benzyl-2,3,4,5,6,7-hexahydro-1,6-methano-1H-4-benzazonine.
Figure 6:
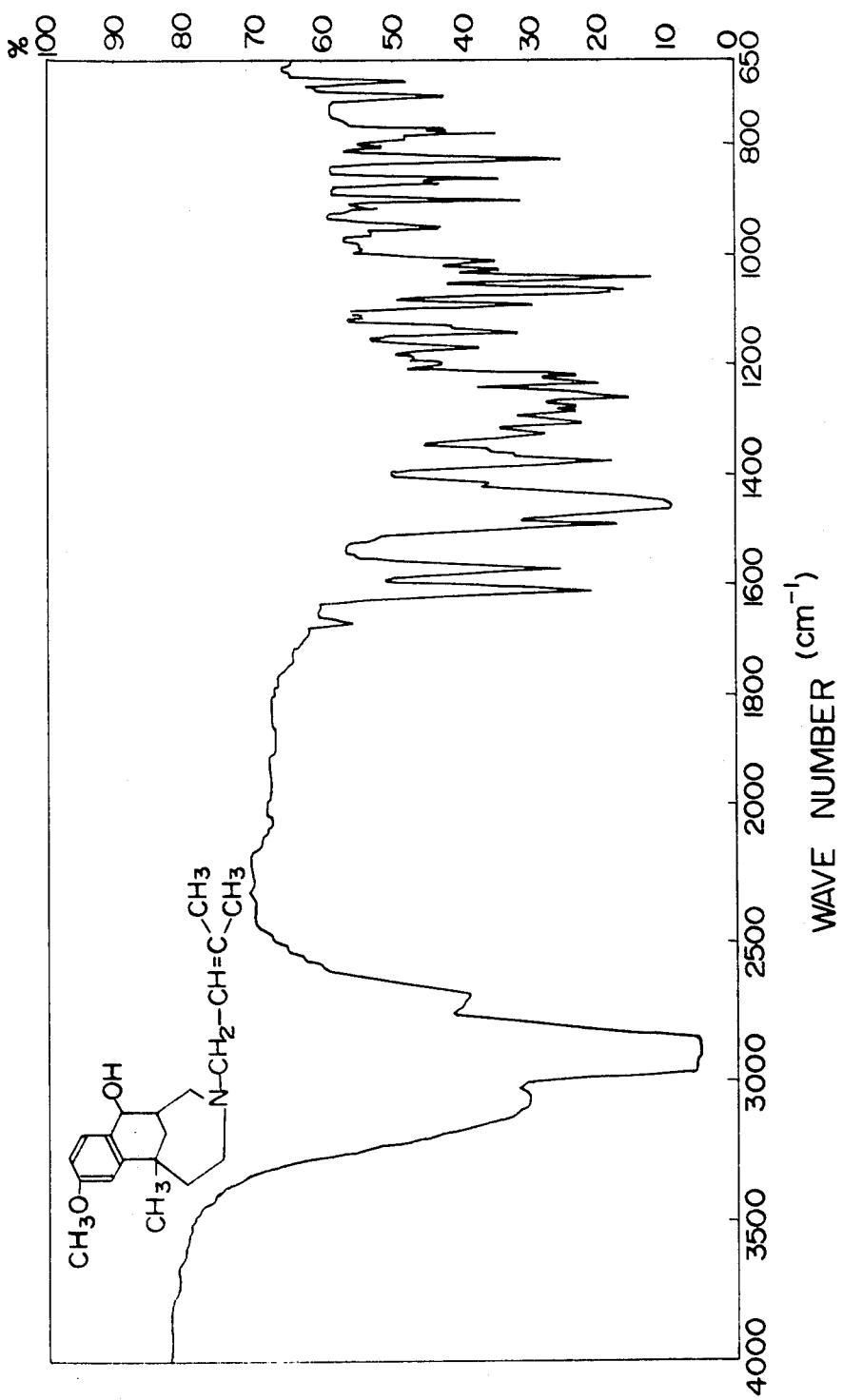
FIG. 6 is an IR spectrum (paste method) of 4-(γ-dimethylallyl)-1-methyl-10-methoxy-2,3,4,5,6,7-hexahydro-1,6-methano-1H-4-benzazonin-7-ol.

25 g of 4-(N-methylaminoethyl)-3,4-dihydronaphthalene-1(2H)-one hydrochloride was dissolved in 400 ml of methanol, and 17g of 37% formalin was added to the solution. The mixture was allowed to stand still at 40° C for 48 hours, and methanol was distilled from the reaction mixture. The residue was made alkaline with sodium hydroxide and extracted with ether. The ether extract was dried and filtered, and ether was distilled from the filtrate. The residual oily product was subjected to vacuum distillation and a fraction boiling at 130° to 137° C under 1.5 mmHg was collected to obtain 13g of a yellow oil. This was 4-methyl-2,3,4,5-tetrahydro-1,6-methano-1H-4-benzazonin-7(6H)-one, and the melting point of the picrate was 176° to 178° C (decomposition).

Example 2 to 8

Reactants indicated in Table III were treated in the same manner as in Example 1 to obtain products shown in Table III. The products had boiling points or melting points shown in Table III.

Table III

| Example No. | Reactant [4-(N-methyl-aminoethyl)-3,4-dihydro-naphthalene-1(2H)-one hydrochloride] | Product | Boiling and Melting Point |
|---|---|---|---|
| 2 | | | b.p. 160–165° C/0.85mmHg<br>m.p. 69–71° C.<br>picrate, m.p.207–209 C.<br>(decomposition) |
| 3 | | | b.p. 170–180° C. (bath temperature)/0.7mmHg |
| 4 | | | b.p. 165–170° C./0.7mmHg<br>m.p. 82–84° C. |
| 5 | | | b.p. 175–185° C. (bath temperature)/0.2mmHg |

Table III-continued

| Example No. | Reactant [4-(N-methyl-aminoethyl)-3,4-dihydro-naphthalene-1(2H)-one hydrochloride] | Product | Boiling and Melting Point |
|---|---|---|---|
| 6 | (structure with $H_3C$, $NHCH_3 \cdot HCl$) | (structure with $H_3C$, $N-CH_3$) | b.p. 130–140° C./1.5mmHg |
| 7 | (structure with $H_3C$, $CH_3$, $NHCH_3 \cdot HCl$) | (structure with $H_3C$, $N-CH_3$) | b.p. 154–156° C.(bath temperature)/1mmHg |
| 8 | (structure with $CH_3$, $NHCH_3 \cdot HCl$) | (structure with $CH_3$, $N-CH_3$) | b.p. 143–146° C./0.5mmHg |

PROCESS FOR SYNTHESIS OF COMPOUND B

Example 9

A solution consisting of 2 g of 4-methyl-2,3,4,5-tetrahydro-1,6-methano-1H-4-Benzazonin-7(6H)-one and 10 ml of methanol was added dropwise to a solution consisting of 1 g of sodium boron hydride and 15 ml of methanol over a period of 30 minutes. The mixture was agitated for 1.5 hours at room temperature, and heated and refluxed for 30 minutes. Methanol was distilled from the reaction mixture liquid and the residue was diluted wth water and then extracted with ether. Ether was distilled from the ether extract and the residue was subjected to vacuum distillation to obtain 1.6 g of a fraction boiling at 155° to 166° C. under 0.7 mmHg. The product was 4-methyl-2,3,4,5,6,7-hexahydro-1,6-methano-1H-4-benzazonin-7-ol. The melting point of the picrate was 214° to 217° C. (decomposition) and the melting point of the hydrochloride was 238° to 242.5° C.

Example 10

6.8 g of 4,12-dimethyl-1-ethyl-10-methoxy-2,3,4,5-tetrahydro-1,6-methano-1H-4-benzazonin-7(6H)-one was dissolved in 400 ml of acetic acid, and 2.5 g of Adams platinum was added to the solution and hydrogenation was carried out at room temperature and atmospheric pressure. The reaction mixture liquid was filtered, and acetic acid was distilled under reduced pressure. The residue was dissolved in water, made alkaline with sodium bicarbonate and extracted with ether. Ether was distilled from the extract and the residue was subjected to vacuum distillation to obtain 6 g of light yellow oil of 4,12-dimethyl-1-ethyl-10-methoxy-2,3,4,5,6,7-hexahydro-1,6-methano-1H-4-benzazonin-7-ol boiling at 215° to 225° C. (bath temperature) under 15 mmHg. The product was converted to a hydrochloride and recrystallized from isopropanol to obtain a white crystal of the trans-1-ethyl-12-methyl type melting at 175° to 185° C. (decomposition). When ether was added to the mother liquid which had been concentrated, a crystal of the cis-1-ethyl-12-methyl type was obtained. This crystal was very hygroscopic.

Examples 11 to 16

Mixtures containing reactants and reducing agents indicated in Table IV were treated in the same manner as in Example 9 to obtain products shown in Table IV. Melting points and boiling points of the products are also shown in Table IV.

Table IV

| Example No. | Reactant [4-benzazonin-7(6H)-one] | Reducing Agent | Product | Boiling or Melting Point | Remarks |
|---|---|---|---|---|---|
| 11 | (structure) | LiAlH₄ | (structure) | m.p.145–147°C hydrochloride, m.p.205–210°C. (decomposition) | |
| 12 | (structure) | LiAlH₄ | (structure) | b.p.200–215°c. (bath temperature)/2mmHg<br>hydrochloride (trans-form), m.p.190–200°C. (decomposition) | hydrochloride(cis-form) being hygroscopic |
| 13 | (structure) | NaBH₄ | (structure) | b.p.200–210°C. (bath temperature)/2.5mmHg<br>hydrochloride, m.p.190–200°C. (decomposition) | |
| 14 | (structure) | NaBH₄ | (structure) | m.p.102–105°C. hydrochloride, m.p. 219–220°C. | |
| 15 | (structure) | NaBH₄ | (structure) | b.p.160–170°C. (bath temperature)/0.5mmHg<br>hydrochloride (trans-form), m.p.205–210°C. (decomposition) | hydrochloride(cis-form) being hygroscopic |
| 16 | (structure) | NaBH₄ | (structure) | b.p. 134–143° C./0.5mmHg | |

PROCESS FOR SYNTHESIS OF COMPOUND C

Example 17

60 g of 57% hydriodic acid, 4.5 g of red phosphorus, 18 ml of water and 25 g of glacial acetic acid were added to 20 g of 1,4-dimethyl-10-methoxy-2,3,4,5,6,7-hexahydro-1,6-methano-1H-4-benzazonin-7-ol, and the mixture was heated and refluxed for 4 hours. The reaction mixture liquid was cooled and filtered, and the filtrate was subjected to distillation under reduced pressure. The residue was dissolved in a small amount of water and neutralized with aqueous ammonia. The precipitated crystal was recovered by filtration, washed with water and dried to obtain 7.8 g of a crystal of 1,4-dimethyl-10-hydroxy-2,3,4,5,6,7-hexahydro-1,6-methano-1H-4-benzazonine. The crystal was dissolved in ethanol and hydrobromic acid was added to the solution. The mixture was treated with fine carbon and filtered. The filtrate was concentrated and ether was added thereto to precipitate a white crystal of the hydrobromide melting at 207° to 210° C.

Example 18

70 g of 57% hydrobromic acid, 5.5 g of red phosphorus and 18 ml of water were added to 17 g of 1,4-dimethyl-2,3,4,5,6,7-hexahydro-1,6-methano-1H-4-benzazonin-7-ol, and the mixture was heated and refluxed for 3 hours. The reaction mixture liquid was cooled and filtered, and the filtrate was subjected to distillation under reduced pressure. The residue was made alkaline with sodium hydroxide and extracted with ether. The ether extract was dried and filtered, and ether was distilled from the extract. The residue was subjected to vacuum distillation to obtain 8 g of 1,4-dimethyl-2,3,4,5,6,7-hexahydro-1,6-methano-1H-4-benzazonine boiling at 160° to 170° C. (bath temperature) under 3 mmHg in the form of a colorless oily product. When the hydrochloride was recrystallized from isopropyl alcohol, the melting point of the recrystallized product was 225° to 230° C.

Examples 19 to 23

Mixtures of reactants and dehydroxylating agents indicated in Table V were treated in the same manner as in Example 17 to obtain products shown in Table V. Boiling or melting points of the products are also shown in Table V.

Table V

| Example No. | Reactant[4-benzazonin-7-ol] | Dehydroxylating Agent | Product | Boiling or Melting Point | Remarks |
|---|---|---|---|---|---|
| 19 | | hydriodic acid red phosphorus water | | b.p. 93–97° C./0.7 mmHg hydrochloride, m.p. 152–154° C. m.p. 249–254° C. | |
| 20 | | hydriobic acid red phosphorus glacial acetic acid water | | hydrobromide (trans-form), m.p. 187–192° C. | cis-form being hygroscopic |
| 21 | | " | | hydrobromide, m.p. 186–190° C. | |
| 22 | | hydrobromic acid red hos horus glacial acetic acid water | | hydrobromide(trans-form), m.p. 175–180° C. | cis-form being hygroscopic |

Table V-continued

| Example No. | Reactant[4-benzazonin-7-ol] | Dehydroxylating Agent | Product | Boiling or Melting Point | Remarks |
| --- | --- | --- | --- | --- | --- |
| 23 | (structure with OH) | " | (structure without OH) | hydrobromide (trans-form), m.p. 187–192° C. | cis-form being hygroscopic |

PROCESS FOR SYNTHESIS OF COMPOUND D (METHOD 4-I(a))

Example 24

1.87 g of 2,3,4,5,6,7-hexahydro-1,6-methano-1H-4-benzazonine, 1.25 g of sodium bicarbonate and 1.33 g of allyl bromide were added into 30 ml of methanol, and the mixture was refluxed for 5 hours and subjected to distillation under reduced pressure. The residue was dissolved in 15 ml of 10% hydrochloric acid. The solution was washed once with 5 ml of benzene, and the water layer was made alkaline with sodium hydroxide and extracted with ether. Ether was distilled from the ether extract and the residue was subjected to vacuum distillation to obtain 2 g of a colorless oily substance as a fraction boiling at 110° to 120° C. (bath temperature) under 0.7 mmHg. The product was dissolved in 15 ml of ether and gaseous hydrochloric acid was blown into the solution to form a white precipitate. The precipitate was recovered by filtration and dried to obtain 4-allyl-2,3,4,5,6,7-hexahydro-1,6-methano-1H-4-benzazonine hydrochloride. Recrystallization from isopropanol gave a white crystalline powder melting at 212.5° to 214.5° C.

SYNTHESIS OF COMPOUND D (METHOD 4-I(b))

Example 25

1.9 g of 2,3,4,5,6,7-hexahydro-1,6-methano-1H-4-benzazonine was dissolved in 20 ml of benzene, and 1.5 g of triethylamine was added to the solution. Then, 1g of acetyl chloride was added dropwise to the mixture under ice cooling and agitation. After completion of the dropwise addition, the reaction mixture liquid was agitated at room temperature for 2 hours and 20 ml of cold 10% hydrochloric acid was added to the mixture. The mixture was agitated, and the benzene layer was separated. The separated benzene layer was washed once with 10 ml of 5% aqueous ammonia, dried and filtered, and benzene was distilled from the filtrate. The residue was dissolved in 20 ml of dioxane, and 0.7 g of lithium aluminum hydride was added to the solution and the mixture was heated and refluxed for 6 hours. The resulting mixture was cooled and several milliliters of water was added thereto. The mixture was extracted with chloroform and chloroform was distilled from the chloroform extract. The residue was subjected to vacuum distillation to obtain 1.3 g of a fraction boiling at 100° to 120° C. (bath temperature) under 0.8 mmHg. The product was a colorless oily substance. The product was dissolved in 3 ml of hydrochloric acid-saturated isopropanol and the solution was cooled with ice to precipitate 4-ethyl-2,3,4,5,6,7-hexahydro-1,6-methano-1H-4-benzazonine hydrochloride in the form of a white crystal. The crystal was recovered by filtration and dried, and when the melting point was determined, it was found that the product had a melting point of 237° to 239° C.

Examples 26 to 42

Reactants indicated in Table VI were treated according to the methods (a), (b) and (c) of the process 4-I disclosed in Examples 25 and 26 and the text of the instant specification, to obtain products shown in Table VI. The melting or boiling points of the products are also shown in Table VI.

Table VI

| Ex. No. | Reactant | Alkyl Halides Acid Halide or Aldehyde | Reducing Agent | Product | Boiling or Melting Point | Remarks |
| --- | --- | --- | --- | --- | --- | --- |
| 26 | (structure with CH$_3$O, CH$_3$, NH) | BrCH$_2$CH=CH$_2$ | | (structure with CH$_3$O, NCH$_2$CH=CH$_2$) | b.p. 155–175° C.(bath temperature)/ 1 mmHgo. | Method (a) |

Table VI-continued
| Ex. No. | Reactant | Alkyl Halides Acid Halide or Aldehyde | Reducing Agent | Product | Boiling or Melting Point | Remarks |
|---|---|---|---|---|---|---|
| 27 | 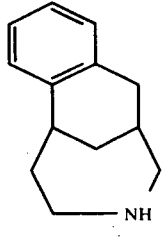 | ClCH₂–C₆H₅ | | 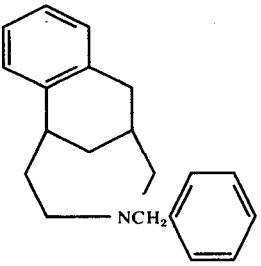 | m.p. 185–191° C. | Method (a) |
| 28 | 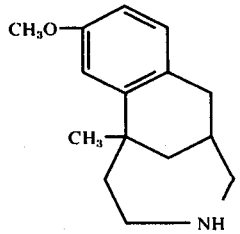 | ClCH₂–C₆H₅ | | 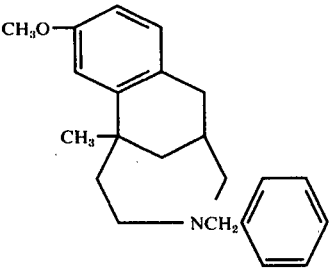 | m.p. 115–125° C. | Method (a) |
| 29 | 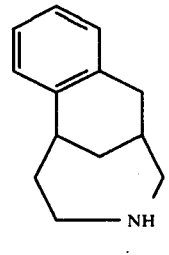 | BrCH₂CH=C(CH₃)₂ | | 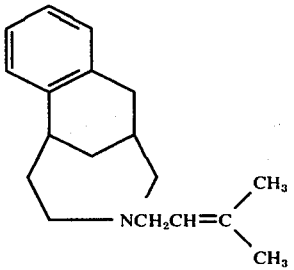 | b.p. 140–150° C.(bath temperature)/ 0.7 mmHg. hydrochloride, m.p. 182–188° C. | Method (a) |
| 30 | 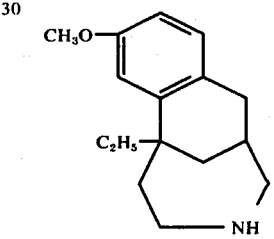 | BrCH₂CH=CH₂ | | 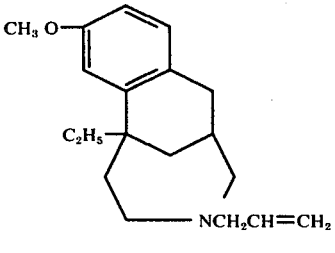 | b.p. 160–180° C./ 1mmHg. | Method (a) |
| 31 | 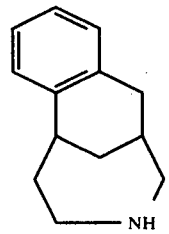 | ClCOCH₂CH(CH₃)₂ | LiAlH₄ | 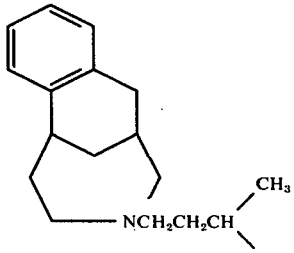 | hydrochloride, m.p. 189–190° C. | Method (b) |

Table VI-continued

| Ex. No. | Reactant | Alkyl Halides Acid Halide or Aldehyde | Reducing Agent | Product | Boiling or Melting Point | Remarks |
|---|---|---|---|---|---|---|
| 32 | (structure: tricyclic amine with NH) | ClCOCH₂–C₆H₅ | LiAlH₄ | (N-CH₂-C₆H₅ product) | hydrochloride m.p. 235–240° C. | Method (b) |
| 33 | (CH₃O-substituted tricyclic amine, CH₃, NH) | ClCOCH₂CH₃ | LiAlH₄ | (NCH₂CH₂CH₃ product) | b.p. 144–145° C./1 mmHg. | Method (b) |
| 34 | (CH₃O-substituted tricyclic amine, CH₃, NH) | ClCOCH₂–C₆H₅ | LiAlH₄ | (N–CH₂CH₂–C₆H₅ product) | m.p. 88–98° C. | Method (b) |
| 35 | (CH₃O-substituted tricyclic amine, CH₃, CH₃, NH) | ClCOCH₃ | LiAlH₄ | (N–CH₂CH₃ product) | hydrochloride (transform), m.p. 172–117° C. | Method (b) |
| 36 | (HO-substituted tricyclic amine, CH₃, NH) | ClCOCH=C(CH₃)₂ | LiAlH₄ | (NCH₂CH=C(CH₃)₂ product) | hydrochloride, m.p. 145–150° C. | Method (b) |
| 37 | (HO-substituted tricyclic amine, CH₃, NH) | ClCOCH₂CH₂CH₃ | LiAlH₄ | (NCH₂CH₂CH₂CH₃ product) | hydrobromide, m.p. 157–158° C. | Method (b) |

Table VI-continued

| Ex. No. | Reactant | Alkyl Halides Acid Halide or Aldehyde | Reducing Agent | Product | Boiling or Melting Point | Remarks |
|---|---|---|---|---|---|---|
| 38 | (structure with NH) | OHC-C₆H₅ | HCOOH | (structure with NCH₂-C₆H₅) | b.p. 165–175° C.(bath temperature)/ 0.7 mmHg. | Method (c) |
| 39 | CH₃O-(structure with CH₃, NH) | ClCOCH₃ | LiAlH₄ | CH₃O-(structure with CH₃, NCH₂CH₃) | hydrochloride, m.p. 190–195° C. | Method (b) |
| 40 | (structure with NH) | ClCOCH₂CH₃ | LiAlH₄ | (structure with NCH₂CH₂CH₃) | b.p. 120–130° C.(bath temperature)/ 0.8 mmHg. hydrochloride, m.p. 222–224° C. | Method (b) |
| 41 | CH₃O-(structure with CH₃, CH₃, NH) | ClCOCH₂-C₆H₅ | LiAlH₄ | CH₃O-(structure with CH₃, CH₃, NCH₂CH₂-C₆H₅) | hydrochloride (trans-form), m.p. 173–178° C. | Method (b) |
| 42 | CH₃O-(structure with CH₃, CH₃, NH) | ClCOCH₂CH₃ | LiAlH₄ | CH₃O-(structure with CH₃, CH₃, N—CH₂CH₂CH₃) | hydrochloride (trans-form), m.p. 157–162° C. | Method (b) |

PROCESS FOR SYNTHESIS OF COMPOUND D (METHOD 4-II)

Example 43

30 ml of ethanol and 3 drops of hydrochloric acid were added to 300 mg of 4-phenethyl-2,3,4,5-tetrahydro-1,6-methano-1H-4-benzazonin-7-(6H)-one, and then, 0.4 g of palladium-carbon (5% palladium) was added to the mixture. The resulting solution was heated at about 70° C. and hydrogen gas was introduced thereinto for 6 hours under shaking at atmospheric pressure to effect the reduction.

The reaction mixture liquid was cooled and filtered, and ethanol was distilled from the filtrate. The residue was dissolved in a small amount of water, and the solution was made alkaline with aqueous ammonia. The released base was extracted with ether. The ether extract was dried with anhydrous potassium carbonate, and ether was distilled and the residue was subjected to vacuum distillation to thereby obtain about 0.2 g of a colorless oily product of 4-phenethyl-2,3,4,5,6,7-hexahydro-1,6-methano-1H-4-benzazonine in the form of a fraction boiling at 180° to 190° C. (bath temperature) under 1 mmHg. The hydrochloride of the product was recrystallized from isopropanol and the recrystallized product was found to have a melting point of 235° to 240° C.

Examples 44 to 47

Reactants and catalysts indicated in Table VII were treated in the same manner as described in Example 43 to obtain products shown in Table VII. The boiling or melting points of the products are also shown in Table VII.

0.625 g of sodium bicarbonate, and the mixture was heated and refluxed. Then, 0.72 g of allyl bromide was gradually added dropwise to the mixture, and the reaction mixture liquid was heated and refluxed for 5 hours. The mixture was then cooled and filtered, and methanol was distilled under reduced pressure from the filtrate. Recrystallization of the residue from cyclohexane gave 0.95 g of 4-allyl-2,3,4,5,6,7-hexahydro-1,6-methano-1H-7-4-benzazonin-ol in the form of a white crystal melting at 98° to 100° C. The product was converted to a hydrochloride and recrystallized from isopropanol. The recrystallized hydrochloride was water soluble and found to have a melting point of 194° to 198° C.

Table VII

| Example No. | Reactant(4-Benzazonine-7(6H)-one) | Catalyst, Solvent and Promotor | Product | Boiling or Melting Point |
|---|---|---|---|---|
| 44 | [structure] | palladium-carbon (5% Pd) glacial acetic acid 75% perchloric acid | [structure] | m.p. 88–98° C. |
| 45 | [structure] | palladium-carbon (5% Pd) ethanol 35% hydrochloric acid | [structure] | b.p 160–180° C. (bath temperature)/ 1 mmHg |
| 46 | [structure] | palladium-carbon (5% Pd) ethanol 35% hydrochloric acid | [structure] | hydrochoride, m.p. 210–214° C. |
| 47 | [structure] | " | [structure] | b.p. 170–200° C. (bath temperature)/ 0.6 mmHg. |

PROCESS FOR SYNTHESIS OF COMPOUND E (METHOD 5-I(a))

Example 48

20 ml of methanol was added to 1g of 2,3,4,5,6,7-hexahydro-1,6-methanol-1H-4-benzazonin-7-ol and

Examples 49 to 58

The reaction was conducted in the same manner as in Example 48 (method 5-I(a)) by employing reactants shown in Table VIII, to obtain results shown in Table VIII.

Table VIII

| Ex. No. | Reactant (4-benzazonine-7-ol) | Alkyl halide | Product | Boiling or Melting Point | Remarks |
|---|---|---|---|---|---|
| 49 | (structure) | BrCH$_2$CH=CH$_2$ | (structure) | m.p. 124–125° C. | method (a) |
| 50 | (structure) | BrCH$_2$CH=CH$_2$ | (structure) | b.p. 170–180° c. (bath temperature)/ 1 mmHg | method (a) |
| 51 | (structure) | BrCH$_2$CH=C(CH$_3$)$_2$ | (structure) | m.p. 134–136° C. | method (a) |
| 52 | (structure) | BrCH$_2$CH=C(CH$_3$)$_2$ | (structure) | m.p. 155–156° C | method (a) |
| 53 | (structure) | BrCH$_2$-cyclopropyl | (structure) | hydrochloride m.p. 178–181° C. (decomposition) | method (a) |
| 54 | (structure) | ClCH$_2$-phenyl | (structure) | m.p. 72–75° C. | method (a) |

Table VIII-continued

| Ex. No. | Reactant (4-benzazonine-7-ol) | Alkyl halide | Product | Boiling or Melting Point | Remarks |
|---|---|---|---|---|---|
| 55 | (structure with CH₃O, CH₃, OH, NH) | ClCH₂—C₆H₅ | (structure with CH₃O, CH₃, OH, NCH₂—C₆H₅) | m.p. 152–153° C. | method (a) |
| 56 | (structure with OH, NH) | ClCH₂CH=C(CH₃)₂ | (structure with OH, NCH₂CH=C(CH₃)₂) | b.p. 140–160° C. (bath temperature)/1 mmHg. | method (a) |
| 57 | (structure with OH, NH) | ClCH₂CH₂OH | (structure with OH, NCH₂CH₂OH) | m.p. 55–58.5° C. | method (a) |
| 58 | (structure with CH₃, CH₃, OH, NH) | ClCH₂CH₂OH | (structure with CH₃, CH₃, OH, N—CH₂CH₂OH) | hydrochloride (trans-form), m.p. 220–227° C. | method (a) |

PROCESS FOR SYNTHESIS OF COMPOUND E (METHOD 5I(b))

Example 59

20 ml of anhydrous toluene was added to 1 g of 2,3,4,5,6,7-hexahydro-1,6-methano-1H-4-benzazonin-7-ol and 2 g of triethylamine, and 1g of phenylacetyl chloride was added dropwise to the mixture over a period of 30 minutes under ice cooling and agitation. After completion of the dropwise addition, the mixture was agitated for 1 hour at room temperature. Then, the reaction mixture liquid was washed twice with 50 ml of ice water, twice with 50 ml of 3% hydrochloric acid and once with 15% sodium hydroxide. The toluene layer was dried with anhydrous sodium sulfate and toluene was distilled therefrom under reduced pressure. The residue was dissolved in 20 ml of anhydrous ether, and the solution was heated and refluxed together with 0.15 g of lithium aluminum hydride powder for 6 hours. Excess lithium aluminum hydride was decomposed with ethyl acetate, and 40 ml of a saturated aqueous solution of Rochelle salt was added and the mixture was shaken. The ether layer was separated and ether was distilled from the ether layer, and the residue was converted to a hydrobromide and recrystallized from isopropanol, to obtain about 0.8 g of 4-phenethyl-2,3,4,5,6,7-hexahydro-1,6-methano-1H-benzazonin-7-ol hydrobromide in the form of a white crystal melting at 203° to 205° C. (decomposition). The product was water-soluble.

Examples 60 to 64

With use of reactants shown in Table IV, the reaction was conducted in the same manner as in Example 59 (method 5-I(b)), to obtain results shown in Table IX.

Table IX

| Ex. No. | Reactant (4-benz-azonin-7-ol) | Acid Halide | Reducing Agent | Product | Boiling or Melting Point | Remarks |
|---|---|---|---|---|---|---|
| 60 | 4-methyl-7-methoxy compound with OH, CH₃, NH | ClCOCH₂(Ph) | LiAlH₄ | N-CH₂CH₂Ph derivative | m.p. 123-126° C | Method (b) |
| 61 | 4-ethyl-7-methoxy compound with OH, C₂H₅, NH | ClCOCH₃ | LiAlH₄ | N-CH₂CH₃ derivative | hydrochloride, m.p. 192-195° C. (decomposition) | Method (b) |
| 62 | 4-ethyl-7-methoxy compound with OH, C₂H₅, NH | ClCOCH₂CH₃ | LiAlH₄ | N-CH₂CH₂CH₃ derivative | hydrochloride, m.p. 180-190° C. (composition) | Method (b) |
| 63 | 4-methyl-5-methyl-7-methoxy compound with OH, CH₃, CH₃, NH | ClCOCH₂—CH₂CH₃ | LiAlH₄ | N-CH₂CH₂CH₂-CH₃ derivative | hydrochloride (trans-form) m.p. 140-150° C. (decomposition) | Method (b) |
| 64 | compound with OH, NH | ClCO-cyclopropyl | LiAlH₄ | N-CH₂-cyclopropyl derivative | hydrochloride, m.p. 192.5-199.5° C. | Method (b) |

PROCESS FOR SYNTHESIS OF COMPOUND E (METHOD 5-II(a))

Example 65

20 ml of ethanol was added to 1 g of 2,3,4,5-tetrahydro-1,6-methano-1H-4-benzazonin-7(6H)-one and 0.63 g of sodium carbonate, and the mixture was heated and refluxed. Then, 0.72 g of allyl bromide was gradually added to the mixture, and the reaction mixture liquid was heated and refluxed for 5 hours. The mixture was cooled and filtered, and methanol and excessive allyl bromide were distilled from the filtrate. The residue was dissolved in 20 ml of methanol and cooled with ice water, and 0.15 g of sodium boron hydride was gradually added to the solution under agitation. Then, the mixture was agitated at room temperature for 2 hours. Methanol was distilled from the reaction mixture, and 15 ml of water was added to the residue and the mixture was shaken sufficiently. Then, the mixture was extracted with ether and the extract was subjected to distillation to remove ether therefrom. The residue was recrystallized from cyclohexane to obtain 0.9 g of 4-allyl-2,3,4,5,6,7-hexahydro-1,6-methano-1H-4-benzazonin-7-ol in the form of a white crystal melting at 98° to 100° C.

The product was converted to a hydrochloride and recrystallized from isopropanol. The melting point of the recrystallized hydrochloride was 194° to 198° C.

PROCESS FOR SYNTHESIS OF COMPOUND E (METHOD 5-II(b))

Example 66

20 ml of anhydrous toluene was added to 1 g of 2,3,4,5-tetrahydro-1,6-methano-1H-4-benzazonin-7(6H)-one and 2 g of triethylamine, and 1 g of phenylacetyl chloride was added dropwise to the mixture over a period of 30 minutes under ice cooling and agitation. After completion of the dropwise addition, the mixture was agitated for 1 hour at room temperature. The reaction mixture liquid was washed twice with 50 ml of water and the toluene layer was dried with anhydrous sodium sulfate and filtered. Toluene was removed from the filtrate by distillation under reduced pressure, and the residue was dissolved in 20 ml of anhydrous dioxane and the solution was heated and refluxed for 6 hours together with 0.3 g of lithium aluminum hydride. Then, excess lithium aluminum hydride was decomposed with drops of ethyl acetate, and 50 ml of saturated aqueous solution of Rochelle salt was added and the mixture was shaken. The resulting solution was extracted with ether, and the ether extract was subjected to distillation to remove ether therefrom. The residue was subjected to vacuum distillation to obtain 0.9 g of a fraction of 4-phenethyl-2,3,4,5,6,7-hexahydro-1,6-methano-1H-4-benzazonin-7ol boiling at 148° to 152° C. (bath temperature) under 1 mmHg. The product was a light-yellow oil.

The hydrobromide of the product was recrystallized. The melting point of the recrystallized hydrobromide was 203° to 205° C. (decomposition).

Examples 67 to 79

Reactants shown in Table X were treated in the same manner as described in Example 65 or 66 (method (a) or (b)), to obtain results shown in Table X.

Table X

| Ex. No. | Reactant (4-benzazonin-7(6H)-one) | Alkyl Halide or Acid Halide | Producing Agent | ProductA | Boiling or Melting Point | Remarks |
|---|---|---|---|---|---|---|
| 67 | (structure) | $BrCH_2CH=CH_2$ | $NaBH_4$ | (structure with $NCH_2CH=CH_2$) | m.p. 117–120° C. | method (a) |
| 68 | (structure) | $BrCH_2CH=CH_2$ | $NaBH_4$ | (structure with $NCH_2CH=CH_2$) | b.p. 170–180° C. (bath temperature)/1 mmHg | method (a) |
| 69 | (structure with $CH_3O$) | $BrCH_2C=CH_2$ | $LiAlH_4$ | (structure with $CH_3O$ and $NCH_2CH=CH_2$) | m.p. 124–125° C. | method (a) |
| 70 | (structure) | $BrCH_2-CH=C(CH_3)_2$ | $NaBH_4$ | (structure with $NCH_2CH=C(CH_3)_2$) | b.p. 140–160° C. (bath temperature/1 mmHg | method (a) |

Table X-continued

| Ex. No. | Reactant (4-benzasonin-7(6H)-one) | Alkyl Halide or Acid Halide | Reducing Agent | Product | Boiling or Melting Point | Remarks |
|---|---|---|---|---|---|---|
| 71 | 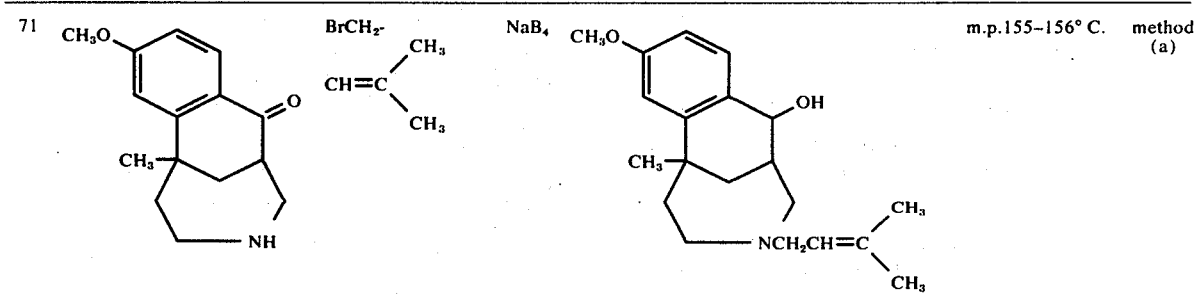 | BrCH$_2$-CH=C(CH$_3$)CH$_3$ | NaB$_4$ | | m.p.155–156° C. | method (a) |
| 72 | 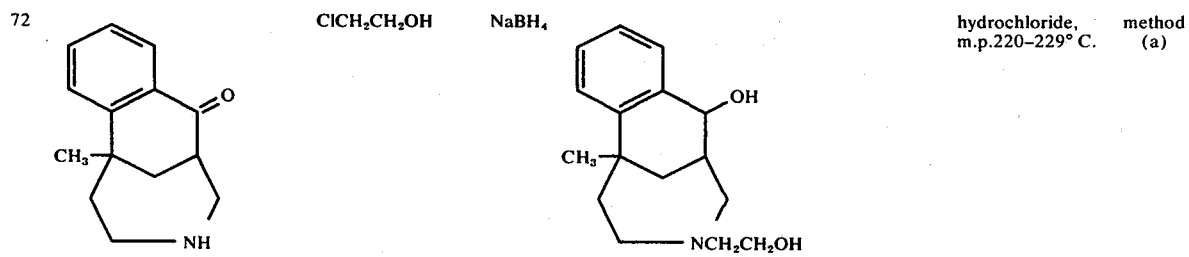 | ClCH$_2$CH$_2$OH | NaBH$_4$ | | hydrochloride, m.p.220–229° C. | method (a) |
| 73 | 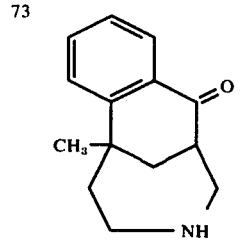 | BrCH$_2$–⊲ | | 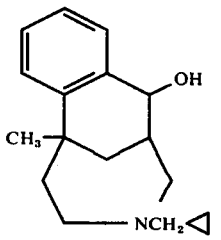 | hydrochloride, m.p.178–181° C. (decomposition) | method (a) |
| 74 | 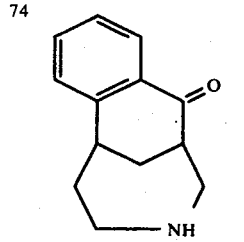 | ClCH$_2$CH$_2$OH | NaBH$_4$ |  | m.p.55–58.5° C. | method (a) |
| 75 | 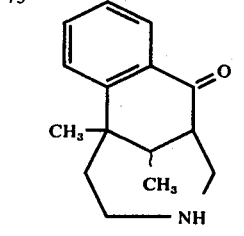 | ClCH$_2$CH$_2$OH | NaBH$_4$ | 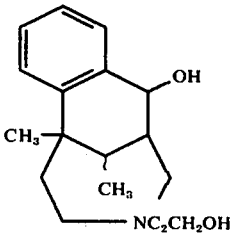 | hydrochloride (trans-form), m.p.220–227° C. | method (a) |
| 76 | 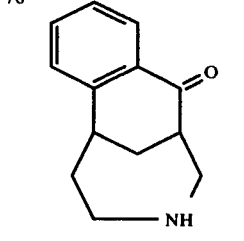 | ClCH$_2$—CH(OH)CH$_2$OH | NaBH$_4$ | 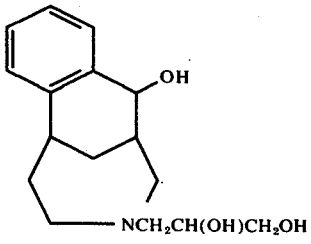 | oil | method (a) |

Table X-continued

| No. | Reactant 1 | Reagent | Product | Notes |
|---|---|---|---|---|
| 77 | (structure: CH₃O-, CH₃-, NH, ketone) | ClCOCH₂–C₆H₅, LiAlH₄ | (structure: CH₃O-, CH₃-, OH, NCH₂CH₂–C₆H₅) | m.p. 123–126° C. method (b) |
| 78 | (structure: CH₃O-, C₂H₅-, NH, ketone) | ClCOCH₂CH₃, LiAlH₄ | (structure: CH₃O-, C₂H₅-, OH, NCH₂CH₂CH₃) | hydrochloride, m.p. 180–190° C, (decomposition) method (b) |
| 79 | (structure: CH₃O-, CH₃-, CH₃-, NH, ketone) | ClCOCH₂CH₂CH₃, LiAlH₄ | (structure: CH₃O-, CH₃-, CH₃-, OH, NCH₂CH₂CH hd 2CH₃) | hydrochloride, (trans-form), m.p. 140–150° C. (decomposition) method (b) |

PROCESS FOR SYNTHESIS OF COMPOUND G

Example 80

A solution consisting of 1.5 g of sodium hydroxide and 5 ml of water was added to a solution consisting of 2.5 g of 4,12-dimethyl-1-ethyl-10-hydroxy-2,3,4,5,6,7-hexahydro-1,6-methano-1H-4-benzazonine and 20 ml of methanol, and the resulting solution was cooled to 0° C. Then, 4 g of nitrosomethylurea was added to the solution and the reaction was conducted at 0° C. for 3 hours. The temperature was returned to room temperature and the reaction mixture was allowed to stand still for 2 hours. Methanol was removed by distillation under reduced pressure, and a small amount of water was added to the residue and the mixture was extracted with ether. When gaseous hydrochloric acid was introduced into the ether extract, there was obtained a white precipitate of 4,12-dimethyl-1-ethyl-10-methoxy-2,3,4,5,6,7-hexahydro-1,6-methano-1H-benzazonine hydrochloride. The precipitate was recovered by filtration and dried to obtain 1.2 g of the product. When it was recrystallized from a liquid mixture of isopropanol and ether, there was obtained 0.4 g of a hydrochloride of the trans-1,12-dimethyl type melting at 172° to 177° C.

Example 81

A solution consisting of 0.8 g of sodium hydroxide and 40 ml of methanol was added to a solution consisting of 4.3 g of trimethylphenyl ammonium bromide and 20 ml of methanol, and the mixture was allowed to stand still. The precipitated crystal was removed by filtration, and the filtrate was incorporated with 2.7 g of 10-hydroxy-1,4,12-trimethyl-2,3,4,5,6,7-hexahydro-1,6-methano-1H-4-benzazonine. The mixture was heated in a water bath to distill methanol therefrom. The residue was heated in an oil bath maintained at 100° to 120° C. for 1 hour to complete the reaction. The reaction mixture was cooled, incorporated with 100 ml of acetic acid and subjected to steam distillation to completely remove dimethylaniline formed as a by-product. Then, the reaction mixture was made alkaline with sodium hydroxide and extracted with ether. When gaseous hydrochloric acid was introduced into the ether extract, there was formed a white precipitate of 10-methoxy-1,4,12-tri-methyl-2,3,4,5,6,7-hexahydro-1,6-methano-1H-4-benzazonine hydrochloride. The precipitate was recovered by filtration and dried to obtain 2 g of the product. When the product was recrystallized from a mixture of isopropanol and ether, 0.8 g of a hydrochloride of the trans-1,12-dimethyl type was obtained. The hydrochloride was found to have a melting point of 185° to 190° C.

Examples 82 to 84

With use of reactants and methoxylating agents indicated in Table XI, the reaction was carried out in the same manner as described in Example 80 or 81, to obtain results shown in Table XI.

Table XI

| Example No. | Reactant (10-hydroxy-4-benzazonine) | Methoxylating Agent | Product | Boiling or Melting Point |
|---|---|---|---|---|
| 82 | (structure) | $CH_2N_2$ | (structure) | hydrochloride, m.p. 215–22° C. |
| 83 | (structure) | $(CH_3)_3N^+Cl^-$ | (structure) | hydrochloride, m.p. 205–210 C. |
| 84 | (structure) | $(CH_3)_3N^+{}_3OS\text{-}C_6H_4\text{-}CH_3$ | (structure) | hydrochloride, m.p. 190–195° C. |

PROCESS FOR SYNTHESIS OF COMPOUND H

Example 85

2 g of 4-(n-butyl)-10-methoxy-1-methyl-2,3,4,5,6,7-hexahydro-1,6-methano-1H-4-benzazonine was dissolved in 30 ml of 47% hydrobromic acid, and the solution was heated and refluxed for about 1 hour. The reaction mixture was cooled and water was distilled under reduced pressure. The residue was dissolved in isopropanol, and a large quantity of ether was added thereto. The resulting mixture was allowed to stand still for a while at room temperature, whereby there was obtained 1.2 g of a white crystal of 4-(n-butyl)-10-hydroxy-1-methyl-2,3,4,5,6,7-hexahydro-1,6-methano-1H-4-benzazonine hydrobromide melting at 157° to 158° C.

Examples 86 to 91

With use of reactants indicated in Table XII, the demethylation was carried out in the same manner as in Example 86, to obtain results in Table XII.

Table XII

| Ex. No. | Reactant (10-Methoxy-4-benzazonine) | Demethylating Agent | Product | Boiling or Melting Point | Remarks |
|---|---|---|---|---|---|
| 86 | (structure) | hydrobromic acid | (structure) | hydrobromide, m.p. 192–195° C. | |

Table XII-continued

| Ex. No. | Reactant (10-Methoxy-4-benzazonine) | Demethylating Agent | Product | Boiling or Melting Point | Remarks |
|---|---|---|---|---|---|
| 87 | [structure: CH₃O-benzazonine with N-CH₂-CH₂-phenyl] | " | [structure: HO-benzazonine with N-CH₂-CH₂-phenyl] | hydrobromide (trans-form), m.p. 175–185° C. | cis-form being hygroscopic |
| 88 | [structure: CH₃O-benzazonine with N-CH₂-cyclopropyl] | " | [structure: HO-benzazonine with N-CH₂-cyclopropyl] | hydrobromide, m.p. 168–171° C. | |
| 89 | [structure: CH₃O-benzazonine with N-CH₂-CH₂-CH(CH₃)₂] | hydrobromic acid | [structure: HO-benzazonine with N-CH₂-CH₂-CH(CH₃)₂] | hydrobromide (trans-form), m.p. 142–153° C. | cis-form being hygroscopic |
| 90 | [structure: CH₃O-benzazonine with N-CH₃] | " | [structure: HO-benzazonine with N-CH₃] | hydrobromide (trans-form), m.p. 187–192° C. | cis-forming being hygroscopic |
| 91 | [structure: CH₃O-benzazonine with N-CH₃] | " | [structure: benzazonine with N-CH₃] | hydrobromide, m.p. 207–210 ° C. | |

PROCESS FOR SYNTHESIS OF COMPOUND J

Example 92

300 ml of ethanol and 3 ml of hydrochloric acid were added to 30 g of 4-methyl-2,3,4,5-tetrahydro-1,6-methano-1H-4-benzazonine-7(6H)-one to form a solution. Then, 50 g of palladium-carbon (5% palladium) was added to the solution, and the solution was heated at about 60° C. and hydrogen gas was introduced thereinto for 6 hours under shaking at atmospheric pressure to effect the reduction. The reaction mixture liquid was cooled and filtered, and ethanol was distilled from the filtrate. The residue was dissolved into 50 ml of water, and the solution was made alkaline by addition of aqueous ammonia and the released base was extracted with ether. The ether extract was dried with anhydrous potassium carbonate, and ether was removed by distillation and the residue was subjected to vacuum distillation. Thus was obtained about 20 g of a colorless oily product of 4-methyl-2,3,4,5,6,7-hexahydro-1,6-methano-1H-4-benzazonine boiling at 93° to 97° C. under 0.7 mmHg. The hydrochloride of the product was recrystallized from isopropanol, and the melting point of the recrystallized hydrochloride was determined. As a result it was found that the recrystallized hydrochloride had a melting point of 252.5° to 254° C. Likewise, the melting point of the hydrobromide of the product was measured and it was found that the hydrobromide had a melting point of 240° to 250° C.

Examples 93 to 98

With use of reactants shown in Table XIII, the reduction was carried out in the same manner as in Example 93, to obtain results shown in Table XIII.

Table XIII

| Ex. No. | Reactant (4-benzazonin-7-one) | Reducing Agent | Product | Boiling or Melting Point |
|---|---|---|---|---|
| 93 | (structure) | glacial acetic acid, 75% perchloric acid, palladium-carbon (5% Pd) | (structure) | b.p. 180–200° C. (bath temperature)/ 4 mmHg hydrochloride, m.p. 205–210° C. |
| 94 | (structure) | glacial acetic acid, 75% perchloric acid, palladium-carbon (5% Pd) | (structure) | b.p. 170–180° C. (bath temperature)/ 2 mmHg. hydrochloride (trans-form), m.p. 185–190° C. |
| 95 | (structure) | methanol, hydrochloric acid, palladium-carbon (5% Pd) | (structure) | b.p. 180–200° C. (bath temperature)/ 3 mmHg. hydrochloride, m.p. 190–195° C. |
| 96 | (structure) | glacial acetic acid, 75% perchloric acid, palladium black | (structure) | b.p. 180–200° C. (bath temperature)/ 2 mmHg. hydrochloride (trans-form), m.p. 172–177° C. |
| 97 | (structure) | glacial acetic acid, 75% perchloric acid, palladium-carbon (5% Pd) | (structure) | b.p. 160–170° C. (bath temperature)/ 3 mmHg. hydrochloride, m.p. 225–230° C. |

Table XIII-continued

| Ex. No. | Reactant (4-benzazonin-7-one) | Reducing Agent | Product | Boiling or Melting Point |
|---|---|---|---|---|
| 98 | 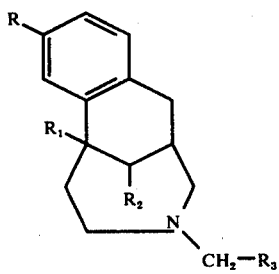 | glacial acetic acid, 75% perchloric acid, palladium-carbon (5% Pd) | 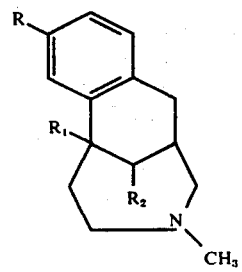 | b.p. 165-175° C. (bath temperature)/ 2 mmHg. hydrochloride (trans-form) m.p. 163-165° C. |

In each of the foregoing Examples, the melting point was measured with use of a micro melting point apparatus.

What we claim is:

1. A compound selected from the group consisting of a 4-benzazonine of the formula:

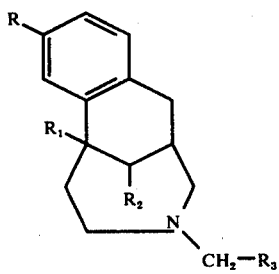

and the pharmaceutically acceptable acid addition salts thereof, wherein R is hydrogen, hydroxy or alkoxy of up to 3 carbon atoms;

$R_1$ is hydrogen or alkyl of up to 3 carbon atoms;
$R_2$ is hydrogen, methyl or ethyl; and
$R_3$ is hydrogen, straight or branched alkyl of up to 4 carbon atoms, straight or branched alkenyl of up to 4 carbon atoms, mono- or dihydroxyalkyl of up to 2 carbon atoms, cycloalkyl of 3 to 6 carbon atoms, phenyl, or phenylmethyl.

2. A compound according to claim 1 wherein R is hydrogen, hydroxy or methoxy;
$R_1$ is alkyl of 1 to 3 carbon atoms;
$R_2$ is hydrogen, methyl or ethyl; and
—$CH_2R_3$ is methyl, ethyl, propyl, butyl, isopentyl, allyl, γ-dimethylallyl, 2-hydroxyethyl, 2,3-dihydroxypropyl, cyclopropylmethyl, benzyl or phenethyl.

3. A compound according to claim 2 which when $R_2$ is other than hydrogen has the cis configuration relative to $R_1$ and $R_2$.

4. A compound according to claim 2 which when $R_2$ is other than hydrogen has the trans configuration relative to $R_1$ and $R_2$.

5. A compound according to claim 2 wherein —$CH_2R_3$ is methyl.

6. A compound according to claim 5 wherein R is methoxy.

7. In the process for the preparation of a compound selected from the group consisting of a 4-benzazonine of the formula:

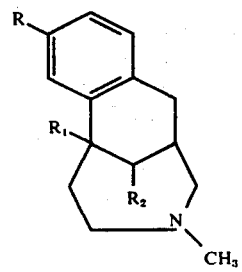

and the pharmaceutically acceptable acid addition salts thereof, wherein
R is hydrogen or hydroxy;
$R_1$ is hydrogen or alkyl of up to 3 carbon atoms; and
$R_2$ is hydrogen, methyl or ethyl; the step which consists essentially of treating a compound of the formula:

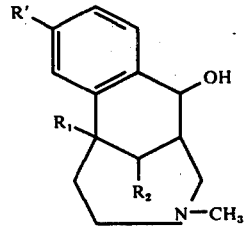

wherein R' is hydrogen or methoxy and each of $R_1$ and $R_2$ are as herein defined with hydriodic acid and red phosphorus.

8. In the process for the preparation of a compound selected from the group consisting of a 4-benzazonine of the formula:

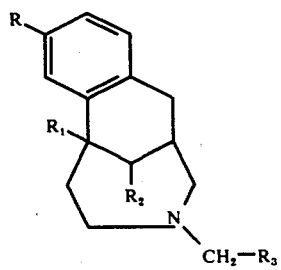

and the pharmaceutically acceptable acid addition salts thereof, wherein

R is hydrogen or alkoxy of up to 3 carbon atoms;
$R_1$ is hydrogen or alkyl of up to 3 carbon atoms;
$R_2$ is hydrogen, methyl or ethyl; and
$R_3$ is hydrogen, straight or branched alkyl of up to 4 carbon atoms, mono- or dihydroxyalkyl of up to 2 carbon atoms, cycloalkyl of 3 to 6 carbon atoms, phenyl or phenylmethyl, the steps which consists essentially of hydrogenating a compound of the formula:

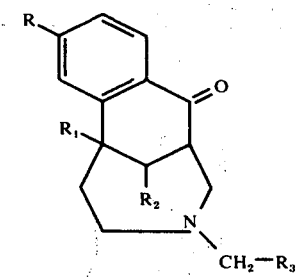

in a polar solvent over a palladium catalyst at a temperature of at least about 50° C.

9. The process according to claim 8 wherein the hydrogenation is conducted in the presence of a strong acid.

10. 1,4-Dimethyl-10-methoxy-2,3,4,5,6,7-hexahydro-1,6-methano-1H-4-benzazonine.

11. 1,4-Dimethyl-10-hydroxy-2,3,4,5,6,7-hexahydro-1,6-methano-1H-4-benzazonine.

12. 1,4-Dimethyl-10-methoxy-2,3,4,5,6,7-hexahydro-1,6-methano-1H-4-benzazonine.

13. 1,4-Dimethyl-2,3,4,5,6,7-hexahydro-1,6-methano-1H-4-benzazonine.

14. 4-(γ-Dimethylallyl)-2,3,4,5,6,7-hexahydro-1,6-methano-1H-4-benzazonine.

15. 4-Allyl-10-methoxy-1-methyl-2,3,4,5,6,7-hexahydro-1,6-methano-1H-4-benzazonine.

16. 10-Methoxy-1-methyl-4-phenethyl-2,3,4,5,6,7-hexahydro-1,6-methano-1H-4-benzazonine.

17. 4-Cyclopropylmethyl-1-methyl-2,3,4,5,6,7-hexahydro-1,6-methano-1H-4-benzazonine.

18. 4-(γ-Dimethylallyl)-10-hydroxy-1-methyl-2,3,4,5,6,7-hexahydro-1,6-methano-1H-4-benzazonine.

* * * * *